US012805903B2

(12) United States Patent
Butki

(10) Patent No.: US 12,805,903 B2
(45) Date of Patent: Nov. 24, 2026

(54) NEEDLE ASSEMBLY WITH REVERBERATION FEATURES TO FACILITATE ULTRASOUND GUIDANCE

(71) Applicant: Andrew J. Butki, Clarkston, MI (US)

(72) Inventor: Andrew J. Butki, Clarkston, MI (US)

(73) Assignee: Andrew J. Butki, Clarkston, MI (US)

( * ) Notice: Subject to any disclaimer, the term of this patent is extended or adjusted under 35 U.S.C. 154(b) by 0 days.

(21) Appl. No.: 19/254,504

(22) Filed: Jun. 30, 2025

(65) Prior Publication Data

US 2025/0325299 A1 Oct. 23, 2025

Related U.S. Application Data

(63) Continuation of application No. 18/609,585, filed on Mar. 19, 2024, now Pat. No. 12,364,504, which is a (Continued)

(51) Int. Cl.
*A61B 17/34* (2006.01)
*A61B 8/00* (2006.01)
(Continued)

(52) U.S. Cl.
CPC ........ *A61B 17/3403* (2013.01); *A61B 8/0841* (2013.01); *A61B 8/481* (2013.01); (Continued)

(58) Field of Classification Search
CPC ............ A61B 10/0233; A61B 17/3403; A61B 2017/3413; A61B 2090/3925; A61B 8/0841; A61B 8/481; A61B 90/39
See application file for complete search history.

(56) References Cited

U.S. PATENT DOCUMENTS 4,072,041 A 2/1978 Hoffman et al.
4,249,539 A 2/1981 Vilkomerson et al.
(Continued)

FOREIGN PATENT DOCUMENTS

DE 3311804 A1 10/1984
JP 5190502 B2 4/2013
(Continued)

OTHER PUBLICATIONS

B. Braun Medical, Inc., Introcan Safety Family of Peripheral IV Catheters, https://www.bbraunusa.com/en/products-and-therapies/infusion-therapy/iv-vascular-and-admixture/introcan-safety.html#, 2018, pp. 1-11.
(Continued)

*Primary Examiner* — Mark D Remaly
(74) *Attorney, Agent, or Firm* — Howard & Howard Attorneys PLLC

(57) ABSTRACT

A needle assembly positionable under visual guidance from an ultrasound system. An elongate body extends distally from a hub along a longitudinal axis and defines a lumen. Reverberation features reverberate incident waves to produce reflected waves to be received by the ultrasound system. The reverberation features may be disposed within the lumen and axially spaced apart from one another along the longitudinal axis. The reverberation features may include opposing portions of an inner surface of a sidewall that define a gap that is smaller or shaped differently than an inner diameter of the lumen. The elongate body may include a solid section near a beveled tip, and the reverberation features are bores defined within the solid section and axially spaced apart from one another. The elongate body may be removably disposed within a sheath in which a distal end of the sheath is axially positioned proximal to the reverberation features.

20 Claims, 30 Drawing Sheets

Related U.S. Application Data continuation of application No. 17/668,846, filed on Feb. 10, 2022, now Pat. No. 11,950,803, which is a continuation of application No. 16/800,631, filed on Feb. 25, 2020, now Pat. No. 11,278,312, which is a continuation-in-part of application No. 16/115,947, filed on Aug. 29, 2018, now Pat. No. 10,966,750.

(51) Int. Cl.
*A61B 8/08* (2006.01)
*A61B 90/00* (2016.01)

(52) U.S. Cl.
CPC ...... *A61B 90/39* (2016.02); *A61B 2017/3413* (2013.01); *A61B 2090/3925* (2016.02)

(56) References Cited

U.S. PATENT DOCUMENTS

| | | | |
|---|---|---|---|
| 4,308,875 | A | 1/1982 | Young |
| 4,401,124 | A | 8/1983 | Guess et al. |
| 4,434,661 | A | 3/1984 | Miwa et al. |
| 4,932,961 | A | 6/1990 | Wong et al. |
| 4,977,897 | A | 12/1990 | Hurwitz |
| 5,383,466 | A | 1/1995 | Partika |
| 5,759,154 | A | 6/1998 | Hoyns |
| 5,769,795 | A | 6/1998 | Terwilliger |
| 6,217,518 | B1 | 4/2001 | Holdaway et al. |
| 7,470,232 | B2 | 12/2008 | Hoctor et al. |
| 8,348,847 | B2 | 1/2013 | Vezina |
| 8,414,495 | B2 | 4/2013 | Halmann et al. |
| 8,747,318 | B2 | 6/2014 | Shiina et al. |
| 8,852,103 | B2 | 10/2014 | Rothberg et al. |
| 9,445,837 | B2 | 9/2016 | Fulton, III |
| 10,966,750 | B2 | 4/2021 | Butki |
| 11,278,312 | B2 | 3/2022 | Butki |
| 11,950,803 | B2 | 4/2024 | Butki |
| 2009/0131790 | A1 | 5/2009 | Munrow et al. |
| 2012/0059247 | A1 | 3/2012 | Speeg et al. |
| 2013/0102899 | A1 | 4/2013 | Vezina |
| 2013/0190609 | A1 | 7/2013 | Fischer, Jr. |
| 2015/0031991 | A1 | 1/2015 | Elfar |
| 2015/0051489 | A1 | 2/2015 | Caluser et al. |
| 2018/0046875 | A1 | 2/2018 | Caluser |
| 2022/0160391 | A1 | 5/2022 | Butki |
| 2024/0216012 | A1 | 7/2024 | Butki |

FOREIGN PATENT DOCUMENTS

| | | | |
|---|---|---|---|
| KR | 101095466 | B1 | 12/2011 |
| WO | 0187177 | A1 | 11/2001 |
| WO | 2016081023 | A1 | 5/2016 |
| WO | 2016148882 | A1 | 9/2016 |
| WO | 2017109080 | A1 | 6/2017 |

OTHER PUBLICATIONS

English language abstract and machine-assisted English translation for JP 5190502 extracted from espacenet.com database on Dec. 13, 2018, 15 pages.
English language abstract and machine-assisted English translation for KR 101095466 extracted from espacenet.com database on Dec. 13, 2018, 14 pages.
English language abstract for DE 3311804 extracted from espacenet.com database on Jun. 5, 2018, 23 pages.
Frantz J. Gibbs, MD, Ultrasound Guidance for Central Venous Catheter Placement, Gibbs & Murphy: Ultrasound-Guided CVC Placement, www.turner-white.com, Mar. 2006, pp. 23-31.
G. Reusz, Needle-related ultrasound artifacts and their importance in anaesthetic Practice, British Journal of Anaesthesia, Feb. 23, 2014, pp. 795-802.
G.A. Chapman, Visualisation of needle position using ultrasonography, Anaesthesia, 2006, 61, pp. 148-158.
Winsberg, Use of an acoustic transponder for US visualization of biopsy needles, Department of Radiology, Mount Sinai Medical Center, City University of New York, NY, Sep. 1991, 180(3), 877-8.
Xia, Ultrasonic Needle Tracking with a Fibre-Optic Ultrasound Transmitter for Guidance of Minimally Invasive Fetal Surgery, Europe PMC Funders Group, Med Image Comput Assist Interv, Sep. 2017, 10434, 637-645.

NEEDLE ASSEMBLY WITH REVERBERATION FEATURES TO FACILITATE ULTRASOUND GUIDANCE

CROSS REFERENCE TO RELATED APPLICATIONS

This is continuation of copending U.S. application Ser. No. 18/609,585, filed Mar. 19, 2024, which is a continuation of U.S. application Ser. No. 17/668,846, filed Feb. 10, 2022, now U.S. Pat. No. 11,950,803, which is a continuation of U.S. application Ser. No. 16/800,631, filed Feb. 25, 2020, now U.S. Pat. No. 11,278,312, which is a continuation-in-part of U.S. application Ser. No. 16/115,947, filed Aug. 29, 2018, now U.S. Pat. No. 10,966,750, each of which is hereby incorporated by reference in its entirety.

BACKGROUND

Percutaneous needle placement is a routine task performed in associated with any number of medical procedures, for example therapy delivery, joint aspiration (arthrocentesis), tissue collection (biopsy), and the like. Of particular interest is vascular access, or obtaining access to a vessel (e.g., vein or artery) for the purpose of intravenous (IV) therapy or blood sampling. Typically, the IV placement of the needle relies on the skill and expertise of the treating medical professional to ensure adequate access while avoiding injury to the surrounding structures. For any number of reasons, IV access may be difficult, for example, inexperience of the treating medical professional and/or unreliable, hidden, collapsed, fragile veins, a phenomena known as difficult venous access (DVA). Also of particular interest is obtaining access to target anatomy for the purpose of performing a subsequent medical task such as tissue biopsy.

Ultrasound guidance is becoming increasingly common in the IV placement of a needle assembly. An ultrasound system includes an ultrasound device, for example a handheld probe, which directs incident waves and receives waves reflected from structures internal to the patient anatomy. Based on assumptions of the speed of sound within tissue, the time delay of the reflected waves is used to create a two-dimensional image of the patient anatomy. FIG. 1 shows the placement of a needle assembly 20 under guidance from an ultrasound device 22 using an "out of plane" technique utilized to view the needle in cross section, and FIG. 2 shows an exemplary output of a display of an ultrasound system. In particular, FIG. 2 shows the cross section of the needle assembly 20, and cross sections of a vein (V) and an artery (A).

It is of critical importance to identify the location of the tip of the needle assembly 20 as it is advancing within the patient anatomy. The known needle assembly of FIGS. 1 and 2, however, is indifferent to this consideration, as it is not specifically identifiable of where along a shaft of the needle assembly 20 is intersecting the incident wave of the ultrasound device 22. As a result, the known arrangement again relies on the skill and expertise of the treating medical professional to coordinate positions of the needle assembly 20 and the ultrasound device 22. Moreover, the representation of the cross section of the needle assembly 20 is often faint or otherwise difficult to visualize due to a variety of factors.

The needle assembly 20 is typically percutaneously advanced at an angle of approach, identified as θ in FIG. 1. With shallower angles of approach, the ultrasound waves reflected from the needle assembly 20 may be generally satisfactory for visualization; however, visualization is less reliable as the angle of approach becomes greater (i.e., steeper).

A known solution is to include removed material (e.g., etchings or indentations) within a sidewall of a needle body having a smooth tubular lumen. For example, U.S. Pat. Nos. 4,401,124 and 9,445,837 disclose features including removed material that purportedly increases the reflectivity of the ultrasound waves. The features require particularly complex geometries, and the reflectivity remains suboptimal at various angles of approach.

Therefore, a need exists in the art for a needle system and methods of positioning a needle assembly within the patient anatomy under visual guidance from the ultrasound system that overcome one or more of the aforementioned disadvantages. There is a further need in the art for an introducer system and methods of positioning an introducer system at target anatomy within the patient under visual guidance from the ultrasound system.

BRIEF DESCRIPTION OF THE DRAWINGS

Advantages of the present disclosure will be readily appreciated as the same becomes better understood by reference to the following detailed description when considered in connection with the accompanying drawings.

SUMMARY

Figure 1:
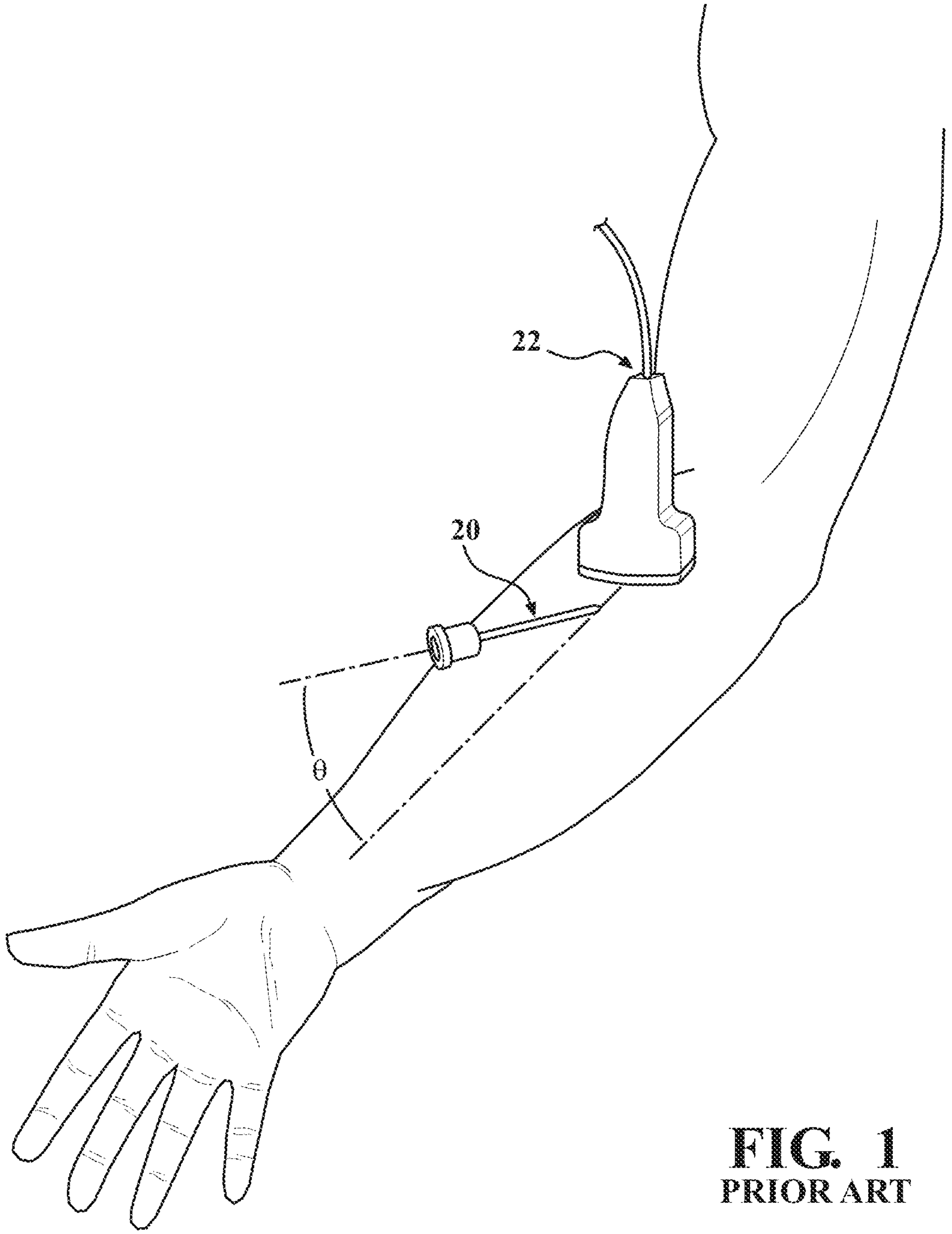
FIG. 1 PRIOR ART
FIG. 1 is a schematic representation of a known needle assembly being percutaneously placed under guidance from an ultrasound device.
Figure 2:
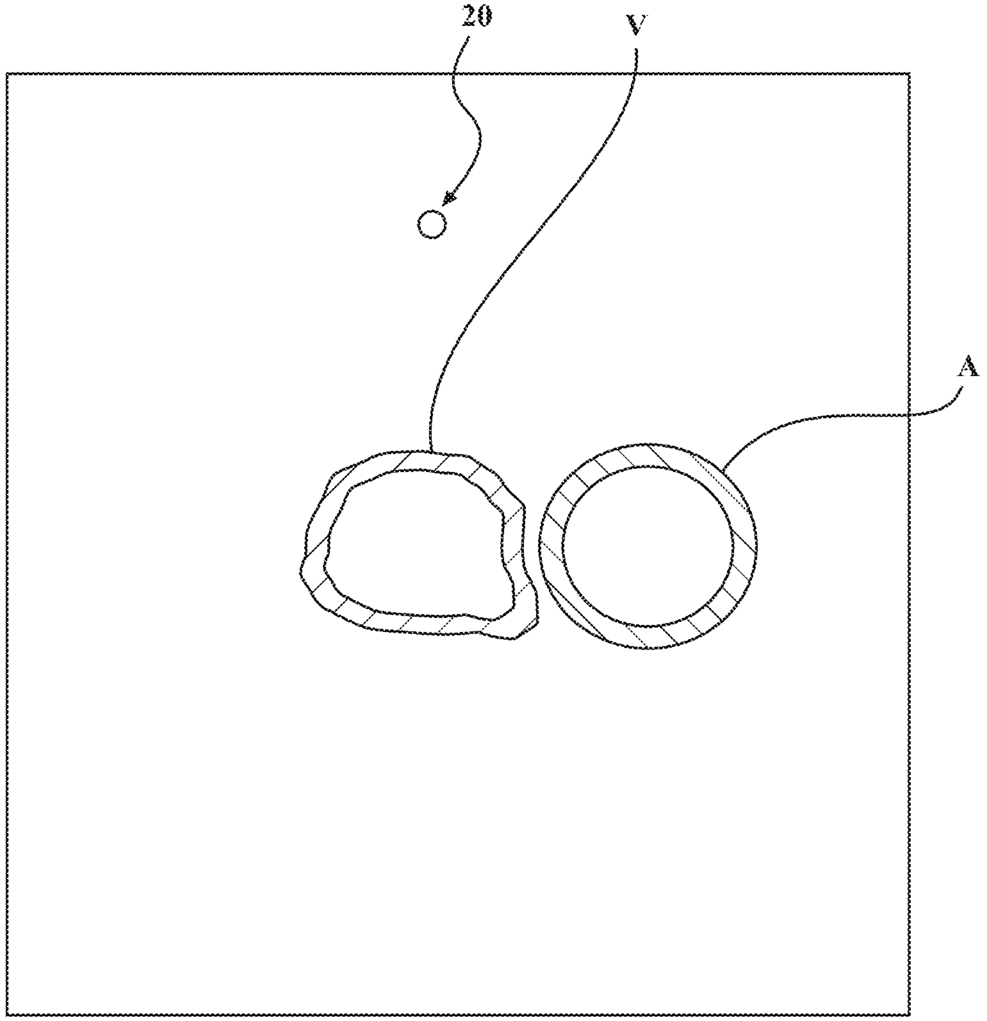
FIG. 2 PRIOR ART
FIG. 2 is a display of an ultrasound system illustrating the output of positioning the known needle assembly of FIG. 2.

According to certain aspects of the present disclosure, an introducer assembly is positionable within anatomy of a patient under visual guidance from an ultrasound system. The introducer assembly includes a sheath and an obturator. The obturator includes an elongate body sized to be removably disposed within the sheath, and a solid section near a distal end that is solid in cross section. A reverberation feature includes a bore extending through the solid section and angled relative to the longitudinal axis. The reverberation feature is configured to reverberate an incident wave within the bore to produce reflected waves. An ultrasound system is configured to direct an incident wave and receive the reflected waves, and generate a visual artifact in response to receiving the reflected waves.

According to certain aspects of the present disclosure, an introducer assembly is positionable within anatomy of a patient under visual guidance from an ultrasound system. The introducer assembly includes a sheath and an obturator. The obturator includes an elongate body sized to be removably disposed within the sheath, and a solid section near a distal end that is solid in cross section. A reverberation feature is defined by a bore or a cavity positioned distal to the sheath and extends from a side to within the solid section. The reverberation feature is configured to reverberate the incident wave within the bore or the cavity to produce the reflected waves. An ultrasound system is configured to direct an incident wave and receive the reflected waves, and generate a visual artifact in response to receiving the reflected waves.

According to certain aspects of the present disclosure, an introducer assembly is positionable within anatomy of a patient under visual guidance from an ultrasound system. The introducer assembly includes a sheath and an obturator. The obturator includes an elongate body sized to be removably disposed within the sheath, and a beveled tip having surfaces tapering to an edge or point. A reverberation feature includes a bore or a cavity extending through the beveled tip. The reverberation feature is configured to reverberate an incident wave within the bore to produce reflected waves. An ultrasound system is configured to direct an incident wave and receive the reflected waves, and generate a visual artifact in response to receiving the reflected waves.

According to certain aspects of the present disclosure, a needle assembly is positionable within anatomy of a patient under visual guidance from an ultrasound system. The needle assembly includes an elongate body having a distal end and a proximal end opposite the distal end. The proximal and distal ends define a longitudinal axis of the elongate body. A sidewall extends between the proximal and distal ends. The sidewall includes an outer surface opposite an inner surface defining a lumen. At least a portion of the lumen includes an inner diameter. The elongate body includes a reverberation feature disposed between the proximal and distal ends. The reverberation feature includes opposing portions of the inner surface of the sidewall defining a gap smaller than the inner diameter of the lumen. The reverberation feature is configured to reverberate an incident wave between the opposing portions to produce reflected waves. The ultrasound system is configured to generate a visual artifact in response to receiving the reflected waves to facilitate the visual guidance.

According to certain aspects of the present disclosure, a needle assembly includes an elongate body having a beveled tip. The beveled tip defines a distal end of the elongate body and configured to penetrate the anatomy of the patient. The beveled tip includes a point defining an inferior aspect of the elongate body, and a heel defining a superior aspect of the elongate body. The elongate body further includes a proximal end opposite the distal end. The distal and proximal ends define a longitudinal axis of the elongate body. The elongate body includes a sidewall extending between the beveled tip and the proximal end. The sidewall includes an outer surface opposite an inner surface defining a lumen. At least a portion of the lumen includes an inner diameter. A reverberation feature includes an upper portion of the inner surface at the superior aspect and a lower portion of the inner surface at the inferior aspect to define a gap shaped differently than the lumen. The upper and lower portions are configured to cooperate to reverberate an incident wave to produce reflected waves. The ultrasound system is configured to generate a visual artifact in response to receiving the reflected waves to facilitate the visual guidance.

According to certain aspects of the present disclosure, a method of positioning a needle assembly within a target anatomy of a patient under visual guidance from an ultrasound system is provided. The needle assembly includes an elongate body, a beveled tip, a sidewall defining a lumen, and a reverberation feature comprising opposing portions of an inner surface of the sidewall defining a gap shaped differently than the lumen. The beveled tip is penetrated through overlying skin surface to direct the needle assembly towards the target anatomy at an angle of approach relative to the overlying skin surface. A probe is positioned external to the overlying skin surface at a location above the target anatomy. The probe is operated to direct an incident wave through the overlying skin surface and towards the target anatomy. At least one of the needle assembly and probe is manipulated such that the incident wave is reverberated with the reverberation feature to generate reflected waves. A visual artifact generated with the ultrasound system based on the reflected waves is viewed on a display.

DETAILED DESCRIPTION

FIGS. 3-10 show a needle assembly 30 in accordance with an exemplary embodiment of the present disclosure. The needle assembly 30 includes an elongate body 32, and in certain embodiments an overlying sheath 34 to be described. The elongate body 32 includes a distal end 36 and a proximal end 38 opposite the distal end 36. The proximal end 38 may extend distally from a hub 40 shown generically in FIG. 3. The hub 40 may be configured coupled to another proximal component (not shown) of the needle assembly 30, for example, a needle safety device, a syringe, a vacuum collection tube, and the like. The elongate body 32 may be rigidly or removably coupled to the hub 40.

Figure 4:
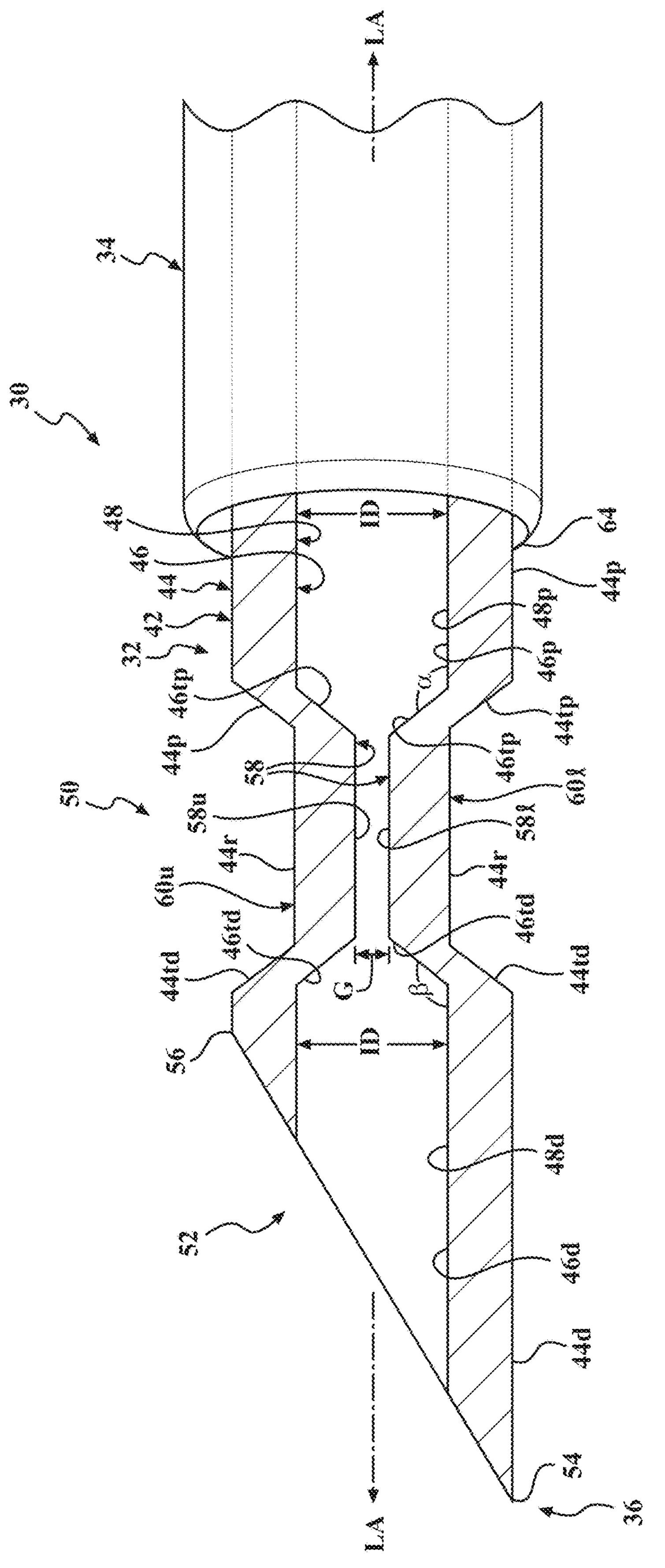
FIG. 4 is a detailed view of the needle assembly of FIG. 3 within rectangle 4-4.

The distal end 36 and the proximal end 38 may define a longitudinal axis (LA) of the elongate body 32, as best shown in FIG. 4. The elongate body 32 includes at least one sidewall 42 extending between the distal and proximal ends 36, 38. The sidewall 42 includes an outer surface 44, and an inner surface 46 opposite the outer surface 44. The inner surface 46 defines a lumen 48 of the elongate body 32. The outer surface 44 may be associated with an outer diameter and the inner surface 46 associated with an inner diameter such that the elongate body 32 is substantially tubular in shape (other than a reverberation feature 50 to be described). Further, the inner and outer surfaces 44, 46 may be oriented parallel to the longitudinal axis (LA) such that the elongate body 32 is substantially straight and tubular in shape. It is contemplated that, in certain variants, the elongate body 32 may be of any suitable cross sectional shape (e.g., triangular, square, rectangular, or a higher-order polygon) and/or include a distal portion curved or angled relative to the longitudinal axis (LA). It is further contemplated that, in certain variants, particularly those with the sheath 34, a portion of the elongate body 32 may be solid in axial section with the exception of the reverberation feature 50. For example, portions proximal and distal to the reverberation feature 50 may be solid in construction.

A beveled tip 52 may define the distal end 36 of the elongate body 32. The beveled tip 52, as appreciated in the art, is configured to penetrate the anatomy of the patient. With concurrent reference to FIGS. 5 and 6, the beveled tip 52 may include a point 54 defining an inferior aspect of the elongate body 32. In other words, the inferior aspect is a bottom of the elongate body 32 when oriented in the manner shown in FIGS. 3 and 4. Likewise, the beveled tip 52 may include a heel 56 defining a superior aspect of the elongate body 32, or a top of the elongate body 32 when oriented in the manner shown in FIGS. 3 and 4. The sidewall 42 extends between the beveled tip 52 and the proximal end 38.

Figure 6:
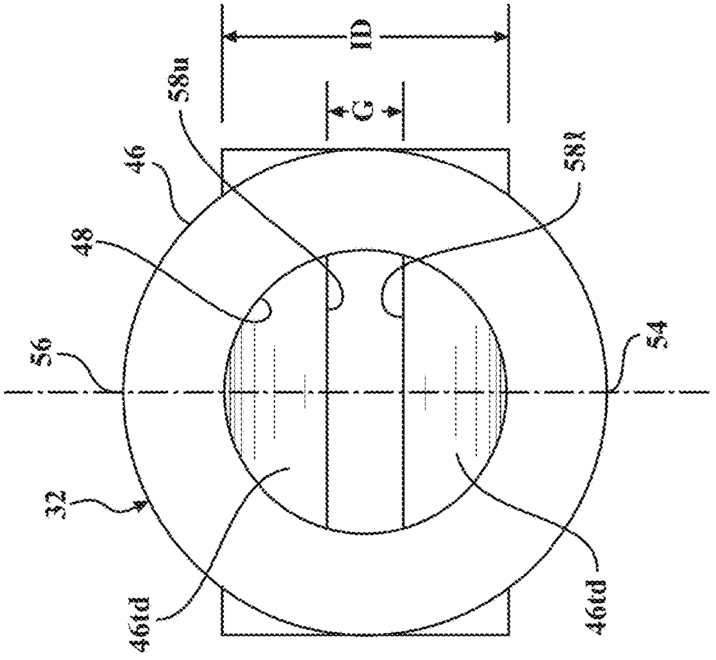
FIG. 6 is an axial view of the needle assembly of FIG. 3.
Figure 5:
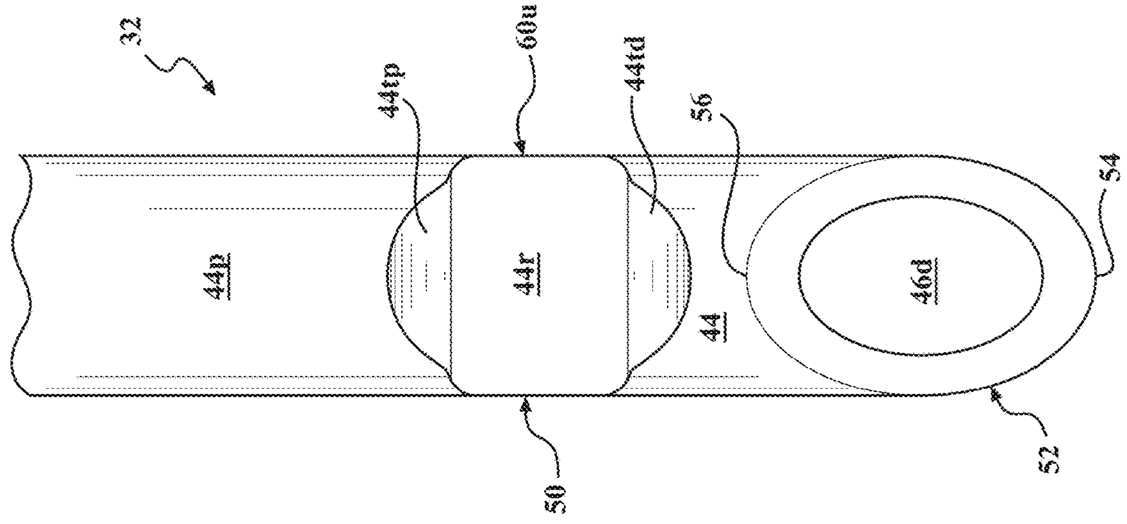
FIG. 5 is a top plan view of the needle assembly of FIG. 3.

The elongate body 32 of the needle assembly 30 includes the reverberation feature 50 disposed between the proximal and distal ends 36, 38. In a manner to be described in detail, the reverberation feature 50, in a broadest sense, is configured to reverberate the incident wave from the probe 23 (see FIG. 20) to produce the reflected waves. As used herein, the term "reverberate" means to reflect the wave(s) (the incident wave(s) and/or one or more of the reflected waves) at least twice as an echo. With reference to FIGS. 4-6, the reverberation feature 50 may include opposing portions 58 of the inner surface 46 of the sidewall 42 defining a gap (G) shaped differently than the inner surface 46 and/or sized smaller than the inner diameter (ID) of the lumen 48. According to one construction, the term "shaped differently" includes an axial sectional profile of the gap (G) defined by a boundary separate than a boundary defined by the inner surface 46 of the sidewall 42. The lumen 48 extending through the elongate body 32 may be defined by at least two portions, including a proximal lumen portion **48*p* defined by a proximal inner surface portion 46*p* and a distal lumen portion 48*d* defined by a distal inner surface portion 46*p*, as shown in FIG. 4. The gap (G) defined between the opposing portions 58 may axially separate and be in fluid communication with the proximal and distal lumen portions 48*p*, 48*d***.

With continued reference to FIG. 4, the inner surface 46 includes the proximal inner surface portion **46*p* defining the proximal lumen portion 48*p* that is tubular in shape. The inner surface 46 may further include at least one proximal transition inner surface portion 46*tp* extending inwardly or towards the longitudinal axis (LA) relative to the proximal inner surface portion 46*p*. The illustrated embodiment shows two proximal transition inner surface portions 46*tp*, one associated with the superior aspect of the elongate body 32 and another associated with the inferior aspect of the elongate body 32. FIG. 4 shows the proximal transition inner surface portion 46*tp* defining an obtuse angle, α, relative to the proximal inner surface portion 46*p*. The angle α may be between 95 and 175 degrees, and more particularly between 100 and 150 degrees, and even more particularly between 105 and 125 degrees. The opposing portions 58 extend distally from the proximal transition inner surface portions 46*tp*. The opposing portions 58 may be opposing planar surfaces oriented parallel to one another to define the gap (G). The arrangement results in the gap (G) being rectangular in axial section and thus shaped differently than the lumen 48 being cylindrical in axial section, as best shown in FIG. 6. In the illustrated embodiment, the opposing planar surfaces are further oriented parallel to the longitudinal axis (LA) of the elongate body 32. In other words, the gap (G) defined between the opposing planar surfaces may be bifurcated by the longitudinal axis (LA), and/or a midline defined between the opposing planar surfaces may be collinear with the longitudinal axis (LA). Extending distally from the opposing portions 58 may be at least one distal transition inner surface portion 46*td* (also shown in the axial view of FIG. 6). The distal transition inner surface portions 46*td* extends outwardly or away from the longitudinal axis (LA) of the elongate body 32. The distal transition inner surface portions 46*td* may be equal in length to the proximal transition inner surface portions 46*tp* such that the inner diameters of the distal and proximal lumen portions 48*p*, 48*d* are equal. The distal inner surface portion 46*d* may extend distally from the distal transition inner surface portions 46*td*. FIG. 4 shows the distal inner surface portion 46*d* defining an obtuse angle, β, relative to the distal transition inner surface portions 46*td*. The angle β may be between 95 and 175 degrees, and more particularly between 100 and 150 degrees, and even more particularly between 105 and 125 degrees. The angle β may be equal to the angle α. The distal inner surface portion 46*d* may defined at least a portion of the beveled tip 52**.

With the elongate body 32 oriented as shown in FIGS. 4 and 6, the opposing portions 58 of the reverberation feature 50 may include an upper portion **58*u* at the superior aspect and a lower portion 58*l* and the inferior aspect. The orientation of FIGS. 4 and 6 may be a preferred orientation of the elongate body 32 as it is percutaneously directed toward target anatomy of the patient based on the structure and function of the beveled tip 52. The arrangement of the upper and lower portions 58*u*, 58*l* may be substantially perpendicular to the incident wave(s) being directed from the ultrasound device 22** to facilitate the ultrasound guidance, as to be described in detail.

The outer surface 44 may be contoured to the inner surface 46 to define the sidewall 42 of substantially constant thickness. For example, FIGS. 4 and 5 show the outer surface 44 including a proximal portion **44*p*, a proximal transition portion 44*tp*, reverberation portions 44*r* corresponding to the opposing portions 58, a distal transition portion 44*td*, and a distal portion 44*d*. The outer surface 44 being contoured to the inner surface 46 may result in one or more crimps 60, more specifically an upper crimp 60*u* and a lower crimp 60*l*. The upper crimp 60*u* may be defined between the upper portion 58*u* of the inner surface 46 and one of the reverberation portions 44*r* of the outer surface 44, and the lower crimp 60*l* may be defined between the lower portion 58*l* of the inner surface 46 and the other one of the reverberation portions 44*r* of the outer surface 44. The crimps 60 of the illustrated embodiment are axially aligned along the longitudinal axis (LA) to define the gap (G). The top plan view of FIG. 5 shows the contour of the outer surface 44 including the upper crimp 60*u***.

Figure 3:
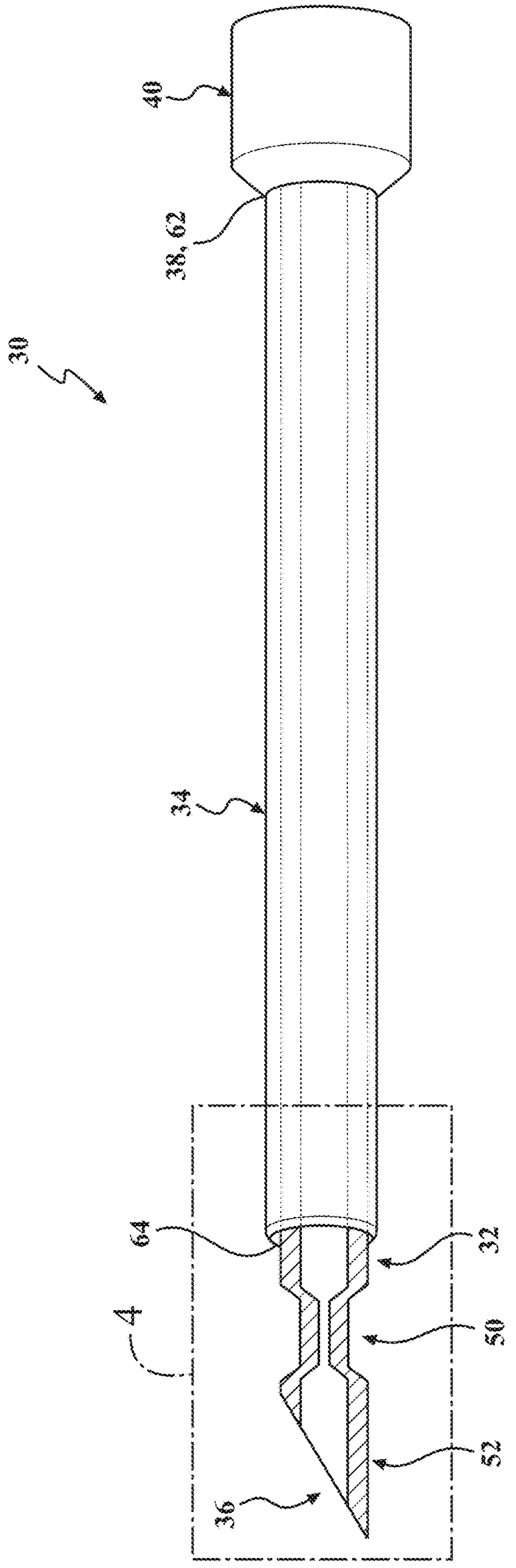
FIG. 3 is a side elevation view of a needle assembly in accordance with an exemplary embodiment of the present disclosure. An elongate body of the needle assembly is shown in section.

As mentioned, it is desirable to identify the location of the distal end 36 of the needle assembly 30 as it is being advanced within the patient anatomy. The reverberation feature 50 is consequently positioned at or near the distal end 36 of the elongate body 32. FIGS. 3-5 best show the reverberation feature 50 positioned immediately proximal to the beveled tip 52. In particular, there is a minimal distance between the heel 56 of the beveled tip 52 and the transition portions **44*td*, 46*td* defining a portion of the reverberation feature 50. It is appreciated that the reverberation feature 50 may be positioned at any suitable location between the proximal and distal ends 36, 38 of the elongate body 32. Further, in embodiments including the sheath 34, the sheath 34 may include a proximal end 62 and a distal end 64, as shown in FIG. 3. The distal end 64 of the sheath 34 may be axially positioned proximal to the reverberation feature 50. Among other advantages, the arrangement prevents interference of the reflected waves with the sheath 34 as the ultrasonic waves are returning or moving towards the ultrasound device 22**.

Figure 9:
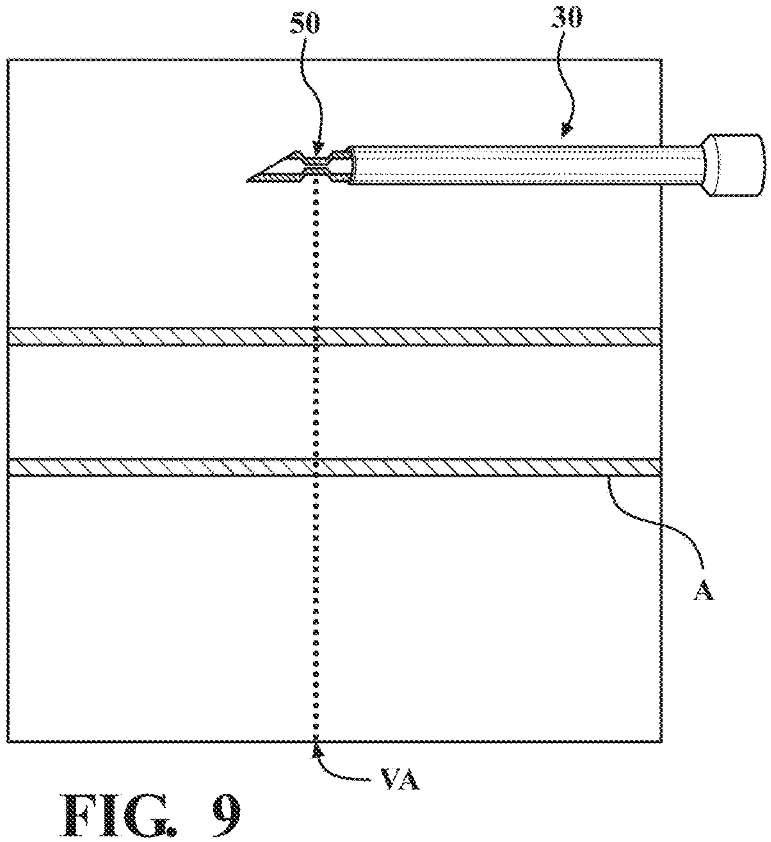
FIG. 9 is a representation of the display of the ultrasound system showing the artifact of FIG. 8 in relation to a side elevation view of the needle assembly and vein.
Figure 10:
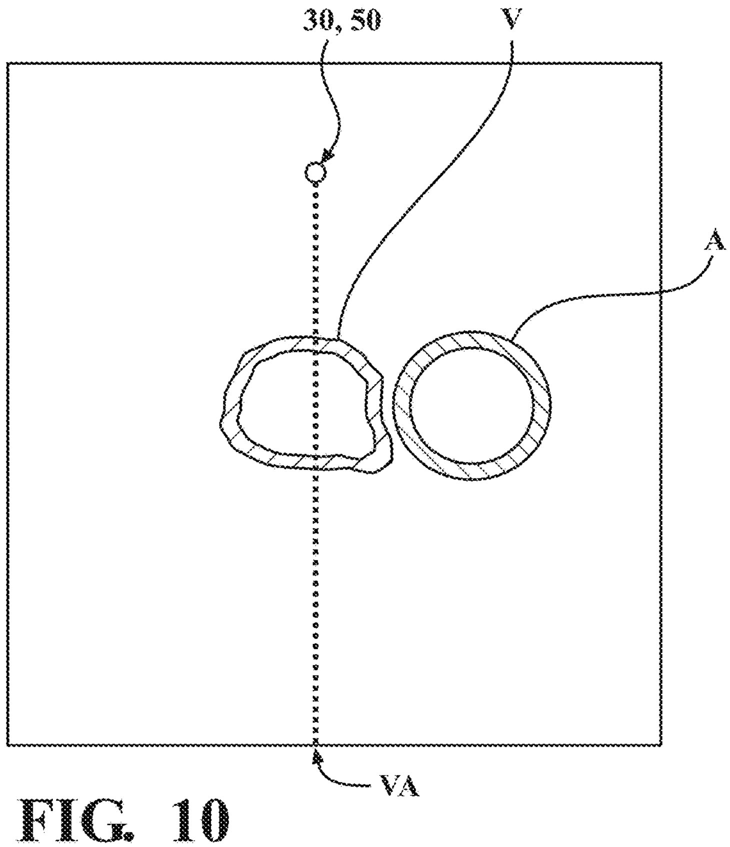
FIG. 10 is a representation of the display of the ultrasound system showing the visual artifact of FIG. 8 in relation to an axial view of the needle assembly and vein.

Operation of the reverberation feature 50 will now be described with reference to FIGS. 7-10. With the needle assembly 30 positioned near the target anatomy, for example superior to the vein (V) as shown in FIGS. 9 and 10, the ultrasound device 22 is operated to direct the incident wave (*) through the target anatomy and the needle assembly 30 positioned therein. While represented as a ray, it should be appreciated that the incident wave (*) may be a two-dimensional beam (B) and its subsequent reverberations (a, b, c, . . . ) may be two-dimensional beams oriented based on the orientation of the ultrasound device 22; e.g., whether an "in plane" or the aforementioned "out of plane" technique is being utilized. The elongate body 32 may be oriented as shown in FIGS. 4 and 6 such that the point 54 of the beveled tip 52 penetrates the anatomy. In such an orientation and depending on an angle of approach θ of the needle assembly 30 and a position of the ultrasound device 22, the opposing portions 58 may be oriented substantially perpendicular to the incident wave (*).

Figure 7:
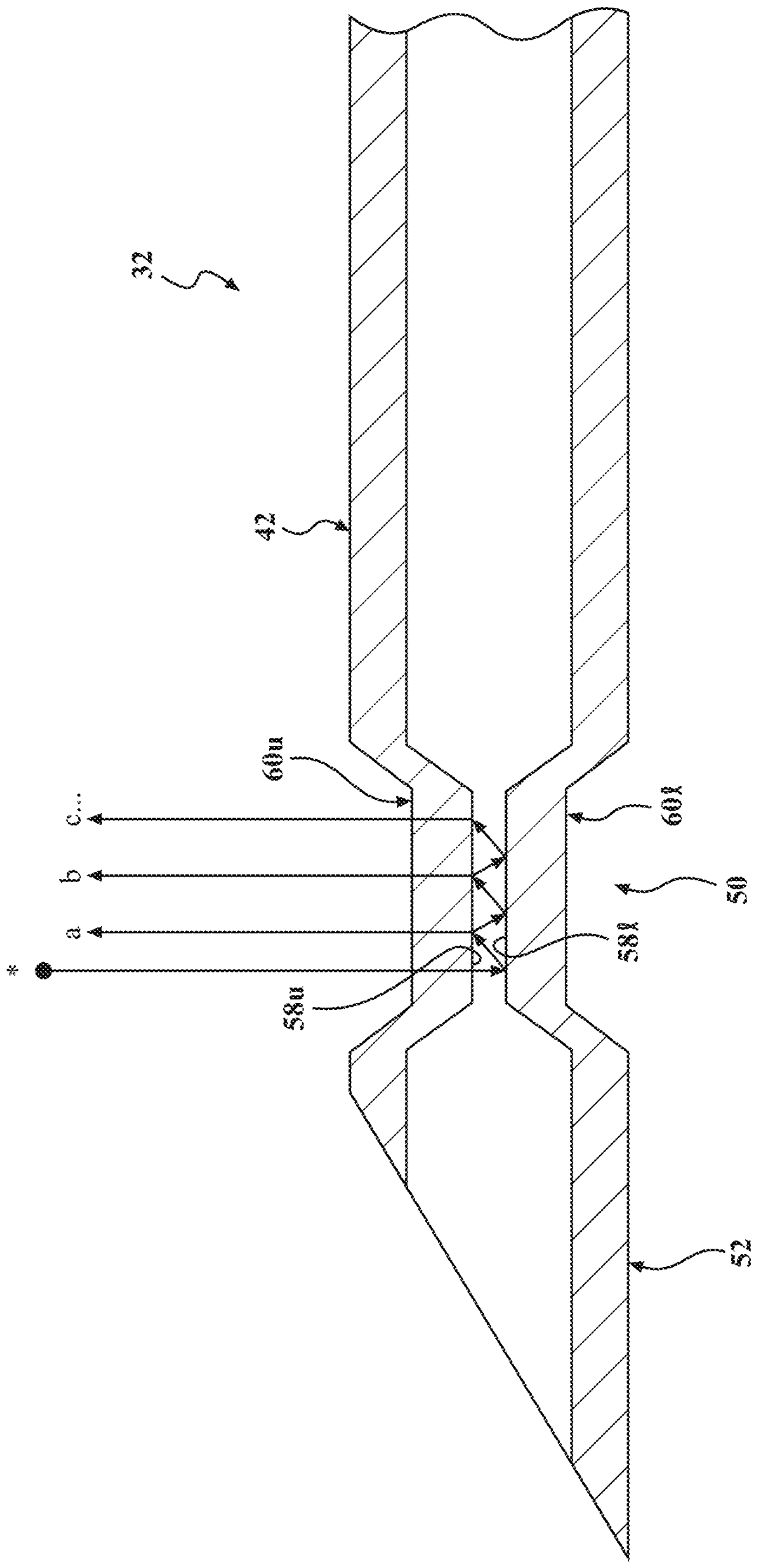
FIG. 7 is a side elevation view of the needle assembly of FIG. 3 with a schematic representation of an incident wave and reflected waves generated by a reverberation feature.
Figure 8:
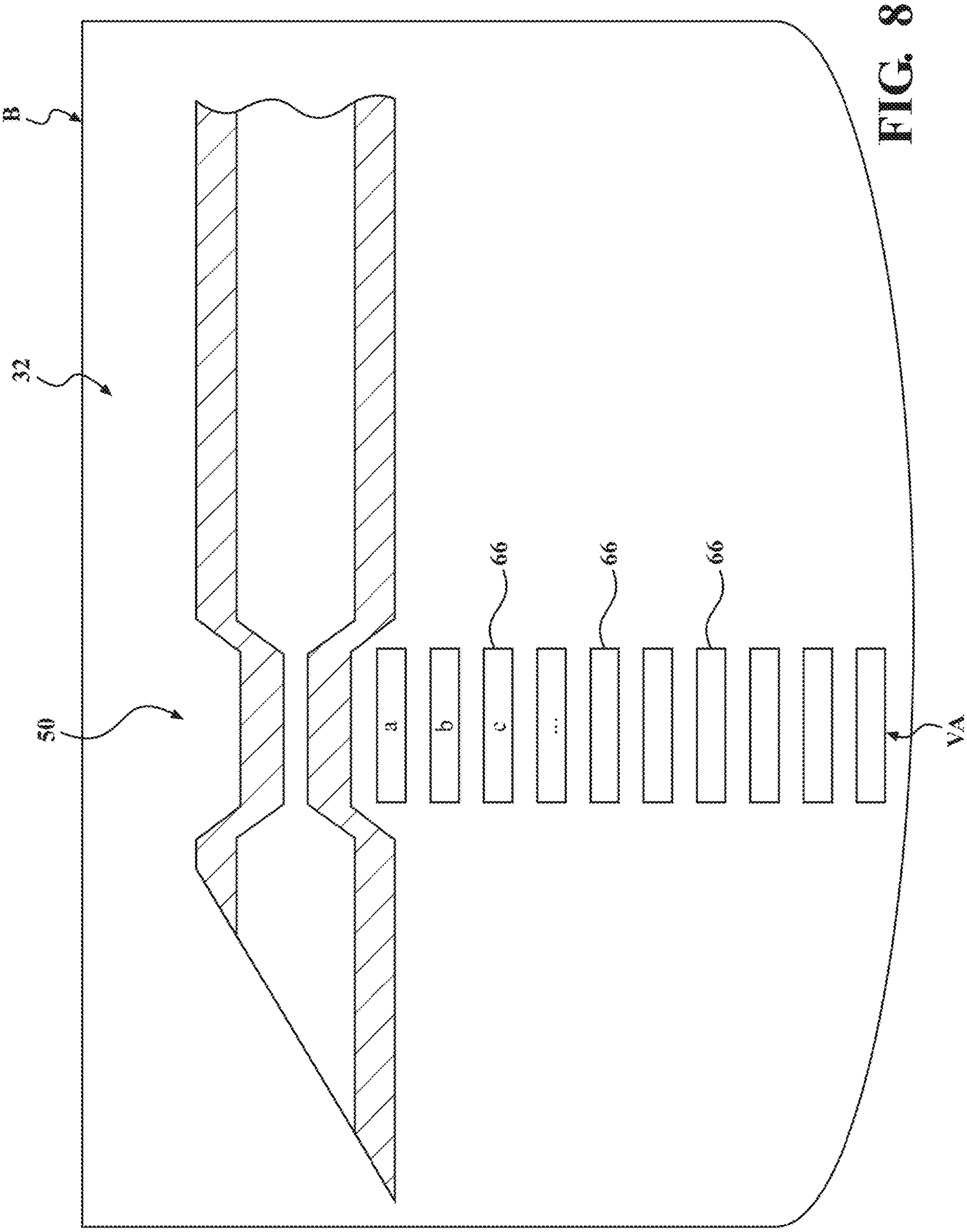
FIG. 8 a side elevation view of the needle assembly of FIG. 3 with a schematic representation of a visual artifact generated by the ultrasound system based on the reflected waves of FIG. 7.

Once the incident wave encounters the reverberation feature 50, and in particular the upper and lower portions **58*u*, 58*l*, the waves reverberate between the opposing portions 58. It is noted that for clarity FIG. 7 shows the reflected waves travelling to the right, yet in reality the incident wave(s) and reflected waves may reverberate in the same axial location. In response to the ultrasound device receiving the reflect waves, with the ultrasound system configured to generate a visual artifact (VA). In particular, the reverberated waves are received by the ultrasound system as echoes with the echoes being reproduced on the display as the visual artifact (VA), for example, a series of bright pixels 66. The visual artifact (VA) may have the appearance of a straight vertical line that begins at the reverberation feature 50 and continuing down the image, as shown in FIGS. 9 and 10, oftentimes seemingly indefinitely (but possibly decaying in brightness). The visual artifact (VA) may be referred to as a ring-down artifact. FIG. 10 shows an axial view of the visual artifact (VA) extending downwardly from the reverberation feature 50 of the needle assembly 30 through the vein (V) adjacent the artery (A). The visual artifact (VA) is distinguishable over known needle assemblies merely purporting to increase reflectivity of the needle body itself. Rather, the needle assembly 30** of the present disclosure utilizes a unique reverberation phenomenon associated with ultrasound technology. It is further noted that, owing to the curvature of a uniform smooth tubular lumen of known needle assemblies, any reflected waves are dispersed or scattered in a multi-directional manner and incapable of resulting in the visual artifact (VA) at angles of approach θ needed for IV placement.

The in-plane technique results in the elevation view of FIG. 9 showing the reverberation feature 50 of the needle assembly 30 positioned superior the artery (A) and the vein (V) is located. Often, discerning whether the vessel is an artery (A) or a vein (V) from the long-axis view using the in-plane technique is often difficult with the anatomical structures appearing as black and tubular in form. The short-axis view of FIG. 10 from the out-of-plane technique is used concurrently for differentiating the artery (A) and the vein (V) based on the relative collapsibility and thickness of the structures. Based on the proximity between the reverberation feature 50 and the distal tip 36, and the continuous imaging provided by a display 26 of the ultrasound system 24 (see FIG. 20), visual guidance is provided to the treating medical professional as she or he locates the distal end 36 of the needle assembly 30 at the target anatomy, for example within the vein (V). (It is noted that the needle assembly 30 would not appear as prominent as shown in FIG. 9, but rather the treating medical professional may rely almost exclusively on the visual artifact (VA) provided by the reverberation feature 50, thereby facilitating improved placement of the distal end 36 of the needle assembly 30.)

Referring now to FIGS. 11-15, the needle assembly 130 in accordance with another exemplary embodiment is shown. In at least some respects, the needle assembly 130 of the present embodiment is the same or similar to that of FIGS. 3-10 with like numerals indicating like components plus one hundred (100). Any abbreviated or omitted description of a like-numerated component is in the interest of brevity and should not be considered absent from the present embodiment. The needle assembly 130 includes an elongate body 132, and in certain embodiments the sheath 134. The elongate body 132 include a distal end 136 and a proximal end (not shown) opposite the distal end 136 and extending distally from a hub (not shown). The elongate body 132 includes at least one sidewall 142 including an outer surface 144, and an inner surface 146 opposite the outer surface 144. The inner surface 146 defines a lumen 148 of the elongate body 132. The outer surface 144 may be associated with an outer diameter and the inner surface 146 associated with an inner diameter such that the elongate body 132 is substantially tubular in shape (other than a reverberation feature 150 to be described). A beveled tip 152 may define the distal end 136 of the elongate body 132 and include a point 154 defining an inferior aspect of the elongate body 132, and a heel 156 defining a superior aspect of the elongate body 132.

Figure 11:
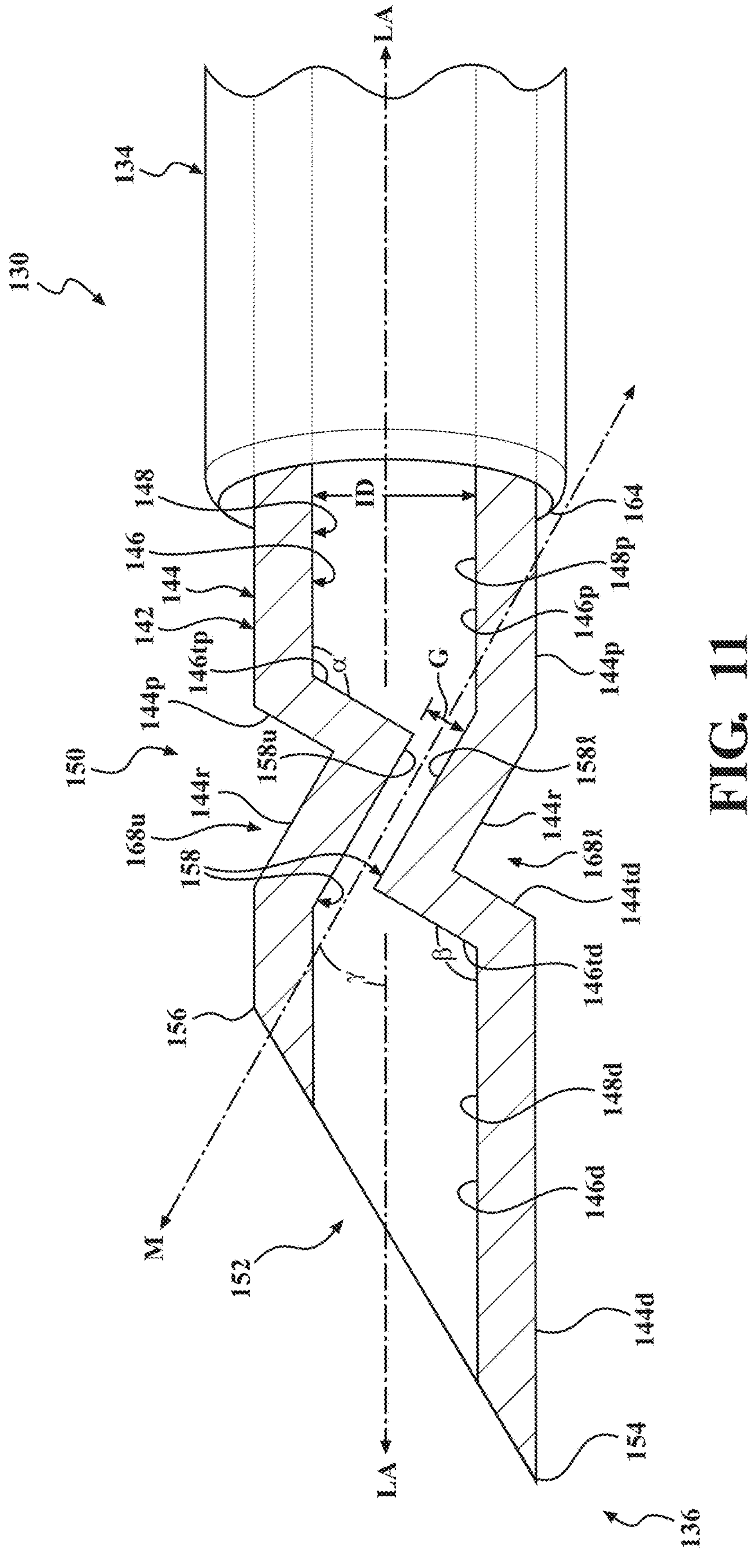
FIG. 11 is a side elevation view of a distal portion of a needle assembly in accordance with another exemplary embodiment of the present disclosure. An elongate body of the needle assembly is shown in section.

The elongate body 132 of the needle assembly 130 includes the reverberation feature 150 disposed between the distal end 136 and the proximal end. The reverberation feature 150 may include opposing portions 158 of the inner surface 146 of the sidewall 142 defining a gap (G) shaped differently than the inner surface 146 and/or sized smaller than the inner diameter (ID) of the lumen 148. The lumen 148 extending through the elongate body 132 may be defined by at least two portions, including a proximal lumen portion **148*p* defined by a proximal inner surface portion 146*p* and a distal lumen portion 148*d* defined by a distal inner surface portion 146*p*, as shown in FIG. 11. The gap (G) defined between the opposing portions 158 may axially separate and be in fluid communication with the proximal and distal lumen portions 148*p*, 148*d***.

With continued reference to FIG. 11, the inner surface 146 includes the proximal inner surface portion **146*p* defining the proximal lumen portion 148*p* that is tubular in shape. The inner surface 146 may further include at least one proximal transition inner surface portion 146*tp* extending inwardly or towards the longitudinal axis (LA) relative to the proximal inner surface portion 146*p*. Whereas the previously described embodiment of the needle assembly 30 included a proximal transition inner surface portion 46*tp* associated with each of the superior and inferior aspects of the elongate body 32, the present embodiment may include a single proximal transition inner surface portion 146*tp*. The illustrated embodiment shows the proximal transition inner surface portion 146*tp* associated with superior aspect of the elongate body 32; however, alternatively the proximal transition inner surface portion 146*tp* may be associated with the inferior aspect of the elongate body 132 (i.e., the reverberation feature 150 is "flipped"). FIG. 11 shows the proximal transition inner surface portion 146*tp* defining an obtuse angle, α, relative to the proximal inner surface portion 146*p***. The angle α may be between 95 and 175 degrees, and more particularly between 100 and 150 degrees, and even more particularly between 105 and 125 degrees.

One of the opposing portions 158 may extend distally from the proximal transition inner surface portion **146*tp*, and another one of the opposing portions 158 may extend distally from the proximal inner surface portion 146*p*. In particular, the opposing portions 158 of the reverberation feature 150 may include an upper portion 158*u* at the superior aspect and extending distally from the proximal transition inner surface portion 146*tp*, and a lower portion 158*l* at the inferior aspect and extending distally from the proximal inner surface portion 146*p*. The opposing portions 158 may be opposing planar surfaces oriented parallel to one another to define the gap (G). The arrangement results in the gap (G) being rectangular in section when viewed along a midline (M) between the opposing portions 158, and thus shaped differently than the lumen 148 being cylindrical in axial section. In the illustrated embodiment, the opposing planar surfaces are further oriented at an angle relative to the longitudinal axis (LA). In particular, the opposing planar surfaces are oriented angularly upward in a proximal-to-distal direction such that the midline (M) between the opposing planar surfaces and the longitudinal axis (LA) define an acute angle, γ, as shown in FIG. 11. The angle γ may be between 5 and 75 degrees, and more particularly between 10 and 60 degrees, and even more particularly between 15 and 45 degrees. The angle γ may correspond to a preferred angle of approach θ of the needle assembly 30 to be directed into the patient anatomy such that the opposing portions 158 are substantially perpendicular to the incident wave(s) being directed from the ultrasound device 22, as to be further described with respect to FIG. 14. In one example of venipuncture for blood sampling, it is often desirable for the angle of approach θ to be approximately thirty degrees, and thus the angle γ may also be approximately thirty degrees such that the opposing portions 158 are substantially horizontal relative to or parallel to the overlying skin surface of the patient against which the ultrasound device 22** may be positioned.

Figure 13:
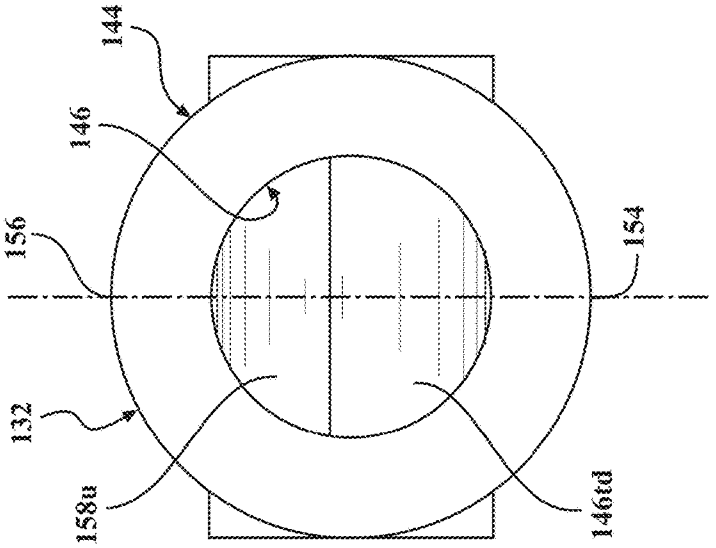
FIG. 13 is an axial view of the needle assembly of FIG. 11.
Figure 12:
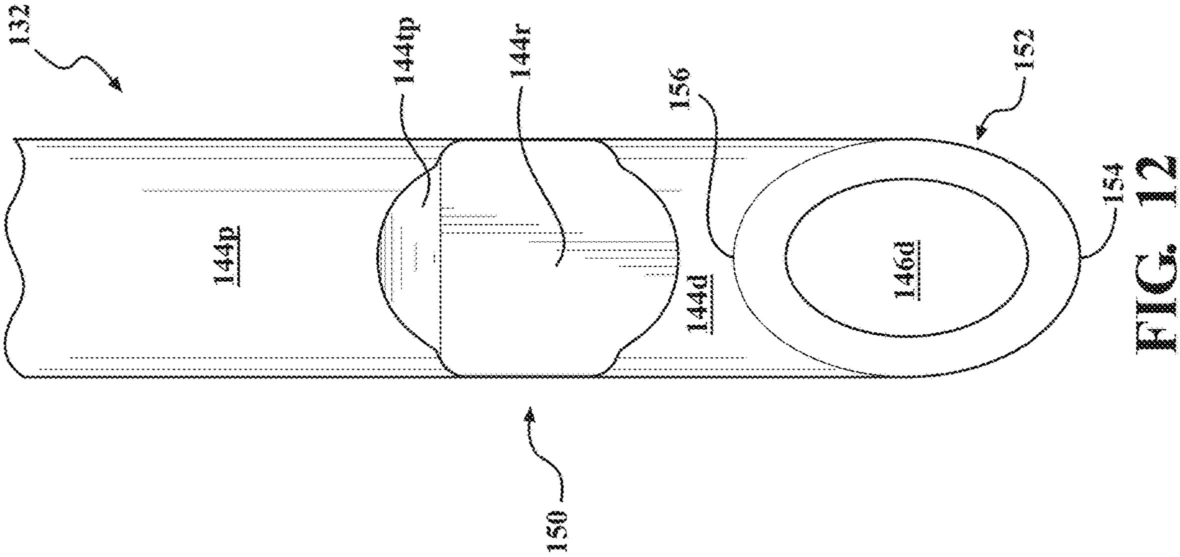
FIG. 12 is a top plan view of the needle assembly of FIG. 11.

Extending distally from one of the opposing portions 158 may be a distal transition inner surface portion **146*td* (also shown in the axial view of FIG. 13). Whereas the previously described embodiment of the needle assembly 30 included a distal transition inner surface portion 46*td* associated with both of the opposing portions 58, the present embodiment may include a single distal transition inner surface portion 146***td*. The illustrated embodiment shows the proximal transition inner surface portion 146*tp* associated with the lower portion 158*l* of the reverberation feature 150; however, alternatively the distal transition inner surface portion 146*td* may be associated with the inferior aspect of the elongate body 132 (i.e., the reverberation feature 150 is "flipped"). The distal transition inner surface portion 146*td* extends outwardly or away from the longitudinal axis (LA) of the elongate body 132. The distal transition inner surface portions 146*td* may be equal in length to the proximal transition inner surface portion 146*tp* such that the inner diameter of the distal and proximal lumen portions 148*p*, 148*d* are equal. The distal inner surface portion 146*d* may extend distally from the distal transition inner surface portion 146*td* as well as the upper portion 158*u* of the reverberation feature 150. FIG. 11 shows the distal inner surface portion 146*d* defining an obtuse angle, β, relative to the distal transition inner surface portion 146*td*. The angle β may be between 95 and 175 degrees, and more particularly between 100 and 150 degrees, and even more particularly between 105 and 125 degrees. The angle β may be equal to the angle α. The distal inner surface portion 146*d* may defined at least a portion of the beveled tip 152.

The outer surface 144 may be contoured to the inner surface 146 to define the sidewall 142 of substantially constant thickness. The illustrated embodiment of FIG. 11 shows the outer surface 144 including a proximal portion 144*p*, a proximal transition portion 144*tp*, reverberation portions 144*r* corresponding to the opposing portions 158, a distal transition portion 144*td*, and a distal portion 144*d*. The outer surface 144 being contoured to the inner surface 146 may result in one or more notches 168, more specifically an upper notch 168*u* and a lower notch 168*l*. The upper notch 168*u* may be defined between the upper portion 158*u* of the inner surface 146 and one of the reverberation portions 144*r* of the outer surface 144, and the lower notch 168*l* may be defined between the lower portion 158*l* of the inner surface 146 and the other one of the reverberation portions 144*r* of the outer surface 144. The illustrated embodiment shows the notches 168 being generally V-shaped when viewed in elevation. The lower notch 168*l* may be complementary to the upper notch 168*u*, and more particularly complimentarily shaped in a manner to be axially spaced apart from the upper notch 168*u* along the longitudinal axis (LA) to define the gap (G). The top plan view of FIG. 5 shows the contour of the outer surface 144 including the upper notch 168*u*.

The reverberation feature 150 may be positioned at or near the distal end 136 of the elongate body 132, for example, immediately proximal to the beveled tip 152. Further, in embodiments including the sheath 134, the sheath 134 may include a distal end 164 axially positioned proximal to the reverberation feature 150.

Figure 14:
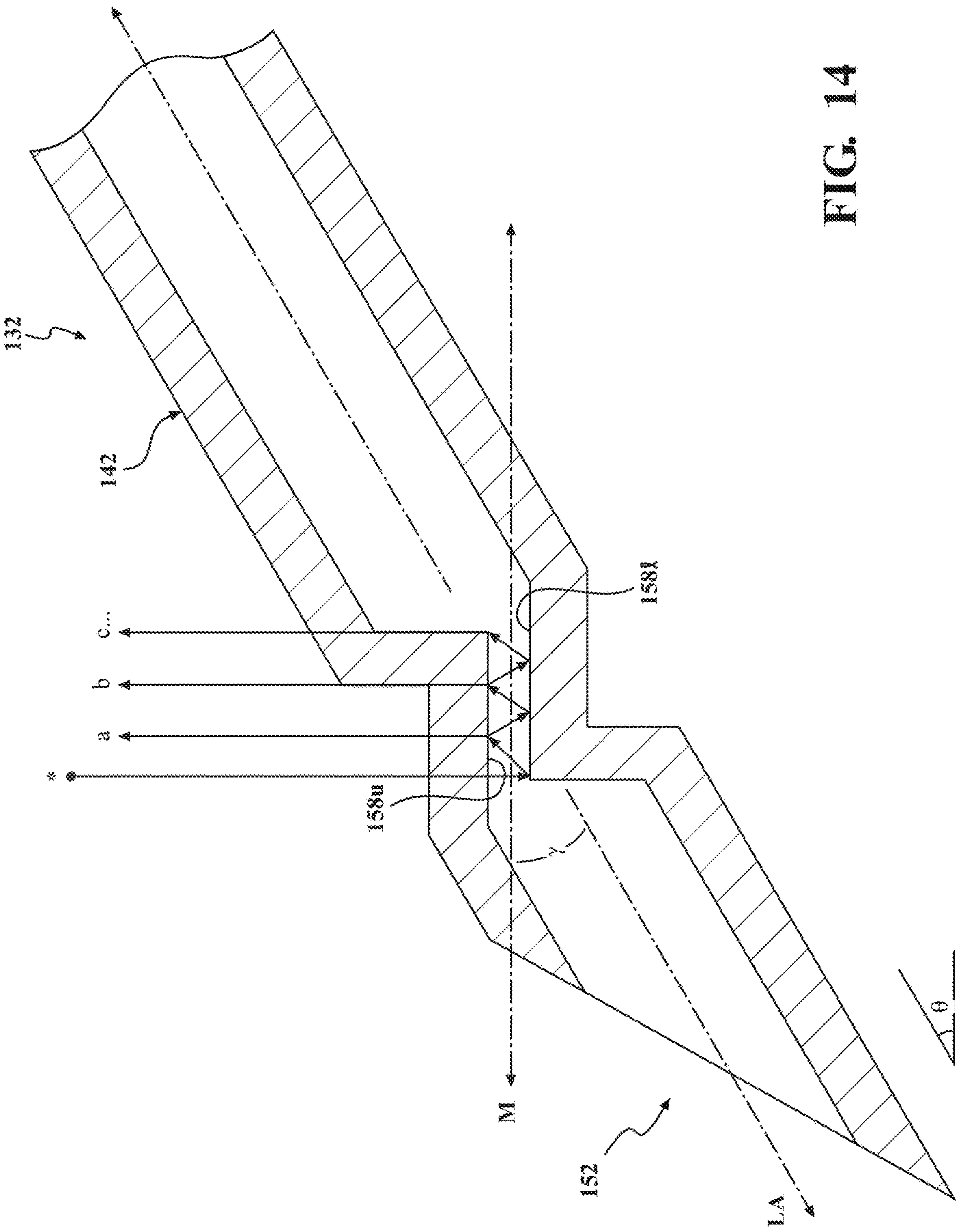
FIG. 14 is a side elevation view of the needle assembly of FIG. 11 positioned at an angle of approach with a schematic representation of an incident wave and reflected waves generated by a reverberation feature.
Figure 15:
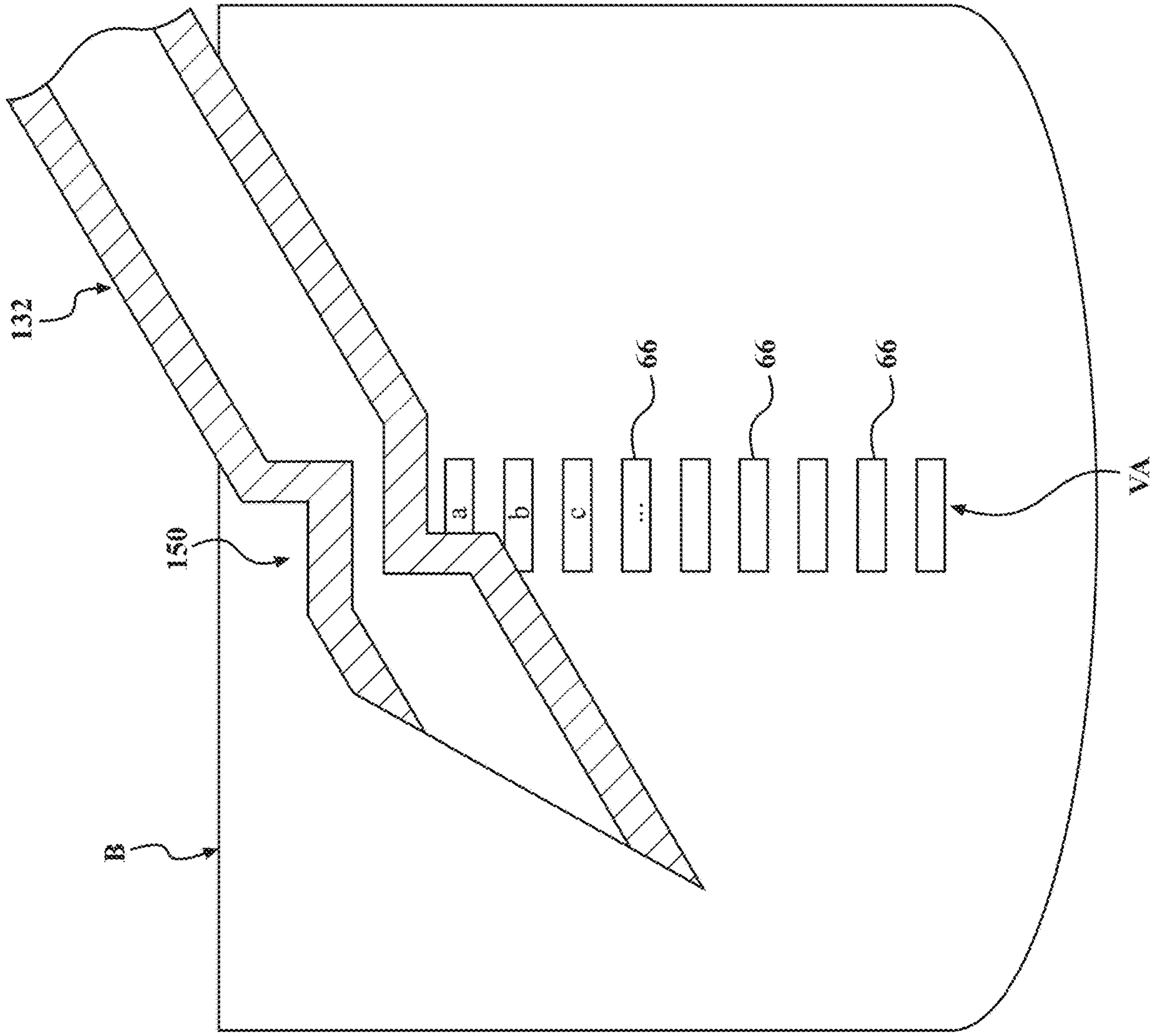
FIG. 15 a side elevation view of the needle assembly of FIG. 13 positioned at the angle of approach of FIG. 14 with a schematic representation of a visual artifact generated by the ultrasound system.

Operation of the reverberation feature 150 will now be described with reference to FIGS. 14 and 15. With the needle assembly 130 is percutaneously advanced and positioned near the target anatomy, for example a vein (V) (see FIGS. 9 and 10). The elongate body 132 may be directed toward and/or positioned within the patient anatomy at the angle of approach θ relative to horizontal or, for example, the overlying tissue of the patient. The angle of approach θ may be any suitable angle but generally is within the range of five to forty-five degrees. In certain embodiments, the angle of approach θ is substantially equal to the angle γ such that the opposing portions 158 are substantially perpendicular to the incident wave (*). Because the opposing portions 158 are substantially perpendicular to the incident wave (*) at the angle of approach θ, the treating medical professional need not significantly orient the ultrasound device 22 relative to the overlying tissue of the patient to produce a visual artifact (VA) to be described. The ultrasound device 22 is operated to direct the incident wave(s) (*) through the target anatomy and the needle assembly 130 positioned therein, and once the incident wave(s) (*) encounter the reverberation feature 150, and in particular the upper and lower portions 158*u*, 158*l*, the waves reverberate between the opposing portions 158. In response to the ultrasound device 22 receiving the reflect waves, with the ultrasound system 24 configured to generate the visual artifact (VA). In particular, the reverberated waves are received by the ultrasound system as echoes with the echoes being reproduced on the display 26 as the visual artifact (VA). Based on the proximity between the reverberation feature 150 and the distal tip 136, and the continuous imaging provided by the ultrasound system 24, visual guidance is provided to the treating medical professional as she or he locates the distal end 136 of the needle assembly 130 at the target anatomy.

Referring now to FIGS. 16-19C, a needle assembly 230 in accordance with another exemplary embodiment is shown. In at least some respects, the needle assembly 230 of the present embodiment is the same or similar to that of FIGS. 3-15 with like numerals indicating like components plus multiples of one hundred (100). Any abbreviated or omitted description of a like-numerated component is in the interest of brevity and should not be considered absent from the present embodiment. The needle assembly 230 includes an elongate body 232, and in certain embodiments an overlying sheath 234. The elongate body 232 includes a distal end 236 and a proximal end (not shown) opposite the distal end 236 and extending distally from a hub (not shown). The elongate body 232 includes at least one sidewall 242 including an outer surface 244, and an inner surface 246 opposite the outer surface 244. The inner surface 246 defines a lumen 248 of the elongate body 232. The outer surface 244 may be associated with an outer diameter and the inner surface 246 associated with an inner diameter such that the elongate body 232 is substantially tubular in shape (other than a reverberation feature 250 to be described). A beveled tip 252 may define the distal end 236 of the elongate body 232 and include a point 254 defining an inferior aspect of the elongate body 232, and a heel 256 defining a superior aspect of the elongate body 232.

Figure 16:
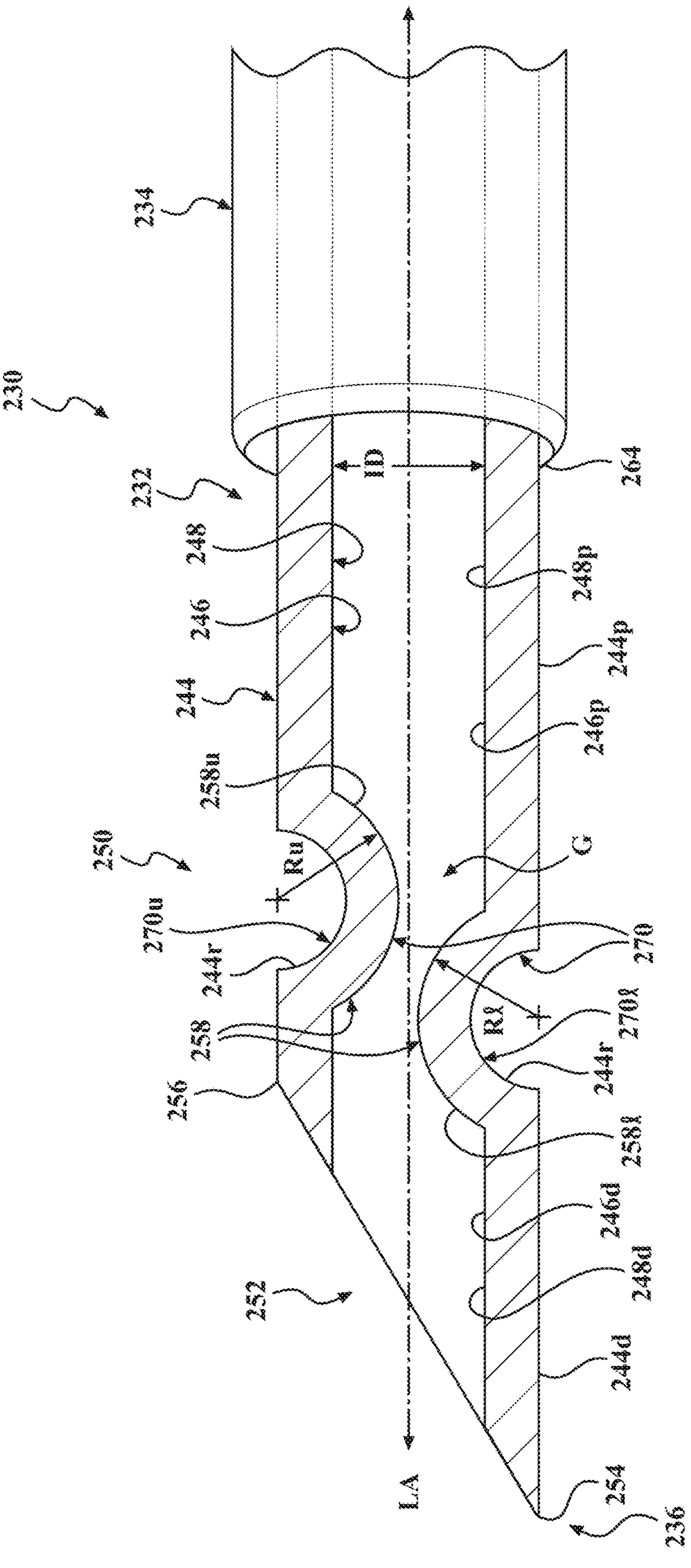
FIG. 16 is a side elevation view of a distal portion of a needle assembly in accordance with another exemplary embodiment of the present disclosure. An elongate body of the needle assembly is shown in section.
Figure 18:
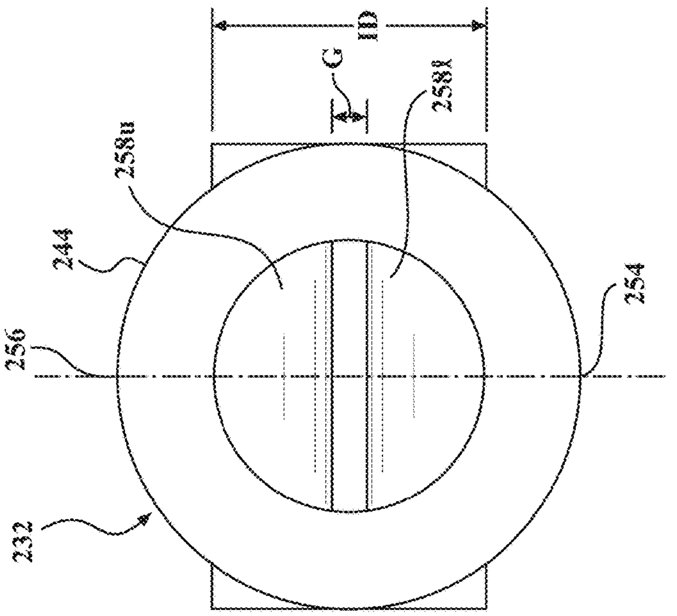
FIG. 18 is an axial view of the needle assembly of FIG. 16.

The elongate body 232 of the needle assembly 230 includes the reverberation feature 250 disposed between the distal end 236 and the proximal end. The reverberation feature 250 may include opposing portions 258 of the inner surface 246 of the sidewall 242 defining a gap (G) shaped differently than the inner surface 246 and/or sized smaller than the inner diameter (ID) of the lumen 248. The lumen 248 extending through the elongate body 232 may be defined by at least two portions, including a proximal lumen portion 248*p* defined by a proximal inner surface portion 246*p* and a distal lumen portion 248*d* defined by a distal inner surface portion 246*p*, as shown in FIG. 16. The gap (G) defined between the opposing portions 258 may axially separate and be in fluid communication with the proximal and distal lumen portions 248*p*, 248*d*.

With continued reference to FIG. 16, the inner surface 246 includes the proximal inner surface portion 246*p* defining the proximal lumen portion 248*p* that is tubular in shape. The opposing portions 258 may extend distally from the proximal inner surface portion 246*p* and extending inwardly or towards the longitudinal axis (LA) relative to the proximal inner surface portion 246*p*. In particular, the opposing portions 258 of the reverberation feature 250 may include an upper portion 258*u* at the superior aspect and a lower portion 258*l* at the inferior aspect. The opposing portions 258 may be arcuate surfaces extending towards the longitudinal axis (LA) to define the gap (G). The arrangement results in the gap (G) being variable in size, and thus shaped differently than the lumen 248 being cylindrical in axial section. In the illustrated embodiment, the opposing arcuate surfaces are semicircular in shape and positioned to at least partially overlap axially along the longitudinal axis (LA). The upper portion 258*u* may include a radius of curvature $R_u$ of between 0.001 and five millimeters, and the lower portion 258*l* may include a radius of curvature $R_y$ of between 0.001 and five millimeters. The radii of curvature $R_u$, $R_l$ of the upper and lower portions 258*u*, 258*l* may be equal, and further may vary based on the dimensions of the elongate body 232 (e.g., the gauge of the needle assembly 230). Extending distally from the opposing portions 258 may be a distal inner surface portion 246*d*. The distal inner surface portion 246*d* may define at least a portion of the beveled tip 252.

Figure 17:
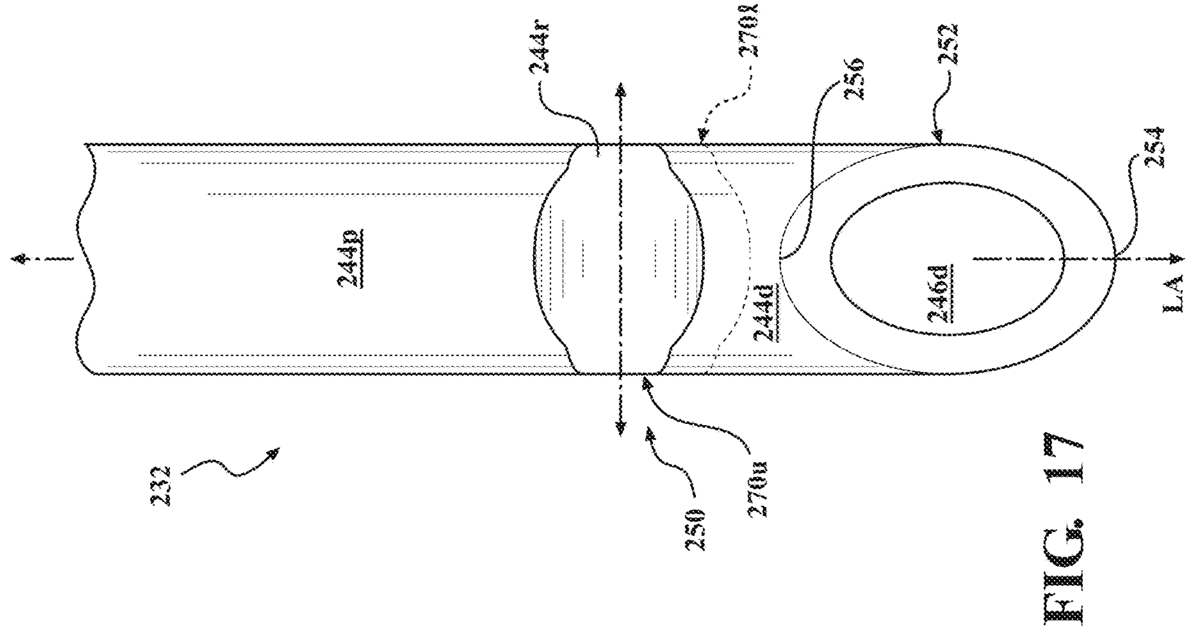
FIG. 17 is a top plan view of the needle assembly of FIG. 16.

The outer surface 244 may be contoured to the inner surface 246 to define the sidewall 242 of substantially constant thickness. The illustrated embodiment of FIG. 16 shows the outer surface 244 including a proximal portion 244*p*, reverberation portions 244*r* corresponding to the opposing portions 258, and a distal portion 244*d*. The outer surface 244 being contoured to the inner surface 246 may result in one or more arcuate protrusions 270, more specifically an upper arcuate protrusion 270*u* and a lower arcuate protrusion 270*l*. The upper arcuate protrusion 270*u* may be defined between the upper portion 258*u* of the inner surface 246 and one of the reverberation portions 244*r* of the outer surface 244, and the lower arcuate protrusion 270*l* may be defined between the lower portion 258*l* of the inner surface 246 and the other one of the reverberation portions 244*r* of the outer surface 244. The illustrated embodiment shows the arcuate protrusions 270 being hemicylindrical in shape and oriented transverse (TR) to the longitudinal axis (LA), as shown in FIG. 17. The lower arcuate protrusion 270*l* may be complementary to the upper arcuate protrusion 270*u*, and more particularly complimentarily shaped in a manner to be axially spaced apart from the upper arcuate protrusion 270*u* along the longitudinal axis (LA) to define the gap (G). The top plan view of FIG. 17 shows the contour of the outer surface 244 including the upper arcuate protrusion 270*u*.

The reverberation feature 250 may be positioned at or near the distal end 236 of the elongate body 232, for example, immediately proximal to the beveled tip 252. Further, in embodiments including the sheath 234, the sheath 234 may include a distal end 264 axially positioned proximal to the reverberation feature 250.

Figure 19A:
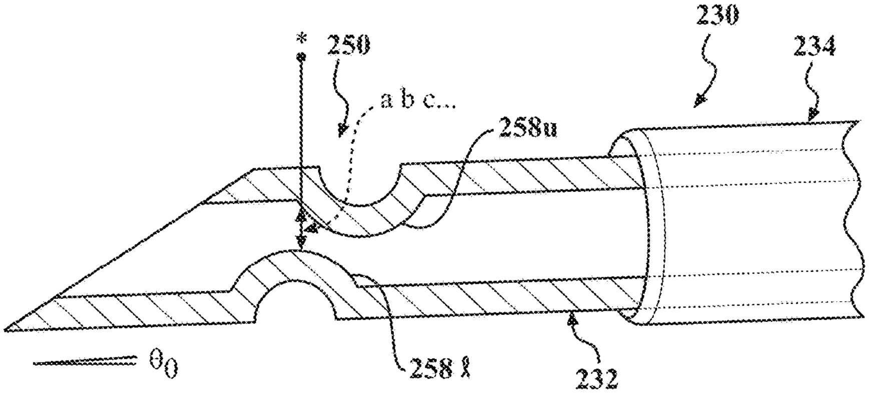
FIG. 19A is a side elevation view of the needle assembly of FIG. 16 positioned at a first angle of approach with a schematic representation of an incident wave and reflected waves generated by a reverberation feature.

Among other advantages, the needle assembly 230 of the present embodiment allows for opposing points on the opposing arcuate portions 258 to be oriented substantially perpendicular to the incident wave (*) throughout a range of angles of approach θ. Operation of the reverberation feature 250 will now be described with reference to FIGS. 19A-19C. With the needle assembly 230 is percutaneously advanced and positioned near the target anatomy, for example a vein (V) (see FIGS. 9 and 10). The elongate body 232 may be directed toward and/or positioned within the patient anatomy at a first angle of approach $\theta_0$ relative to horizontal or, for example, the overlying tissue of the patient. The first angle of approach $\theta_0$ may be relatively shallow, for example, between one and five degrees. Owing to the axial spacing and the complementary radii of curvature $R_u$, $R_l$ of the upper and lower portions 258*u*, 258*l*, a point on each of the upper arcuate surface and the lower arcuate surface is perpendicular to the incident wave(s) (*) (and the reflected wave(s) (a, b, c, . . . )), as shown in FIG. 19A. The ultrasound device 22 is operated to direct the incident wave(s) (*) through the target anatomy and the needle assembly 230 positioned therein, and the waves reverberate between the opposing portions 258. In response to the ultrasound device receiving the reflected waves, with the ultrasound system configured to generate a visual artifact (VA). Based on the proximity between the reverberation feature 250 and the distal tip 236, and the continuous imaging provided by the ultrasound system 24, visual guidance is provided to the treating medical professional as she or he locates the distal end 216 of the needle assembly 230 at the target anatomy.

Figure 19B:
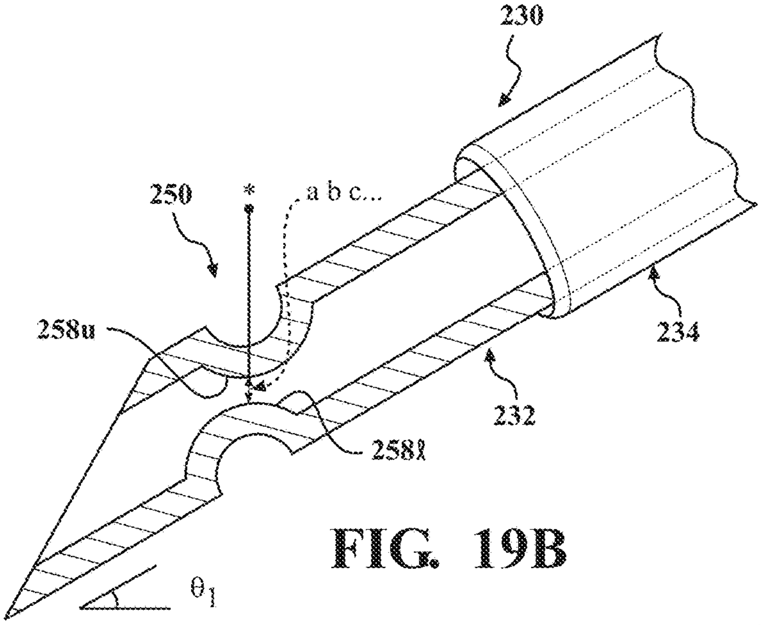
FIG. 19B is a side elevation view of the needle assembly of FIG. 16 positioned at a second angle of approach with a schematic representation of an incident wave and reflected waves generated by a reverberation feature.

The elongate body 232 may be directed toward, positioned, and/or repositioned within the patient anatomy at a second angle of approach $\theta_1$ relative to horizontal or, for example, the overlying tissue of the patient. The second angle of approach $\theta_1$ may be greater than (i.e., steeper) the first angle of approach $\theta_0$. Owing to the axial spacing and the complementary radii of curvature $R_u$, $R_y$ of the upper and lower portions 258*u*, 258*l*, a point on each of the upper arcuate surface and the lower arcuate surface is perpendicular to the incident wave(s) (*) (and the reflected wave(s) (a, b, c, . . . )), as shown in FIG. 19B, without needing to adjust the ultrasound device 22 positioned above the overlying tissue. Likewise, the elongate body 232 may be directed toward, positioned, and/or repositioned within the patient anatomy at a third angle of approach $\theta_2$ relative to horizontal or, for example, the overlying tissue of the patient. The third angle of approach $\theta_2$ may be greater than (i.e., steeper) the first and second angles of approach $\theta_0$, $\theta_1$. Again, owing to the axial spacing and the complementary radii of curvature $R_u$, $R_l$ of the upper and lower portions 258*u*, 258*l*, a point on each of the upper arcuate surface and the lower arcuate surface is perpendicular to the incident wave(s) (*) (and the reflected wave(s) (a, b, c, . . . )), as shown in FIG. 19BC without needing to adjust the ultrasound device 22 positioned above the overlying tissue. As a result, the waves reverberate between the opposing portions 258 through a range of angles of approach θ, and thus visual artifact (VA) remains displayed throughout the range of angles of approach θ without needing to adjust the ultrasound device 22. The range of angles of approach θ from which the present embodiment of the needle assembly 230 is capable of reverberating the waves may be between 1 and 85 degrees, more particularly between 5 and 75 degrees, and even more particularly between 10 and 65 degrees. Such an embodiment of the needle assembly 230 may be particularly well suited with the ultrasound device 22 coupled to the anatomy of the patient, thereby freeing one of the hands of the treating medical professional for other tasks of the medical procedure.

Figure 19C:
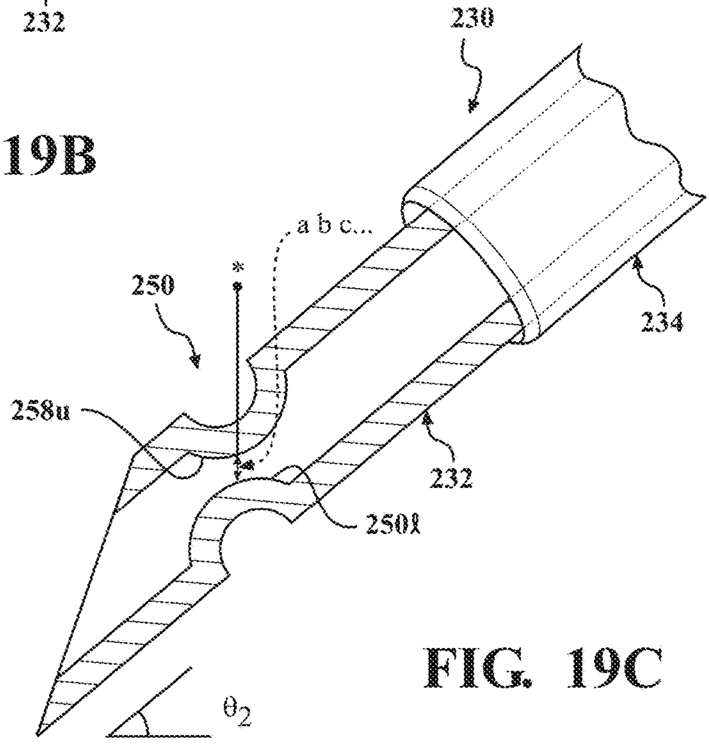
FIG. 19C is a side elevation view of the needle assembly of FIG. 16 positioned at a third angle of approach with a schematic representation of an incident wave and reflected waves generated by a reverberation feature.
Figure 20:
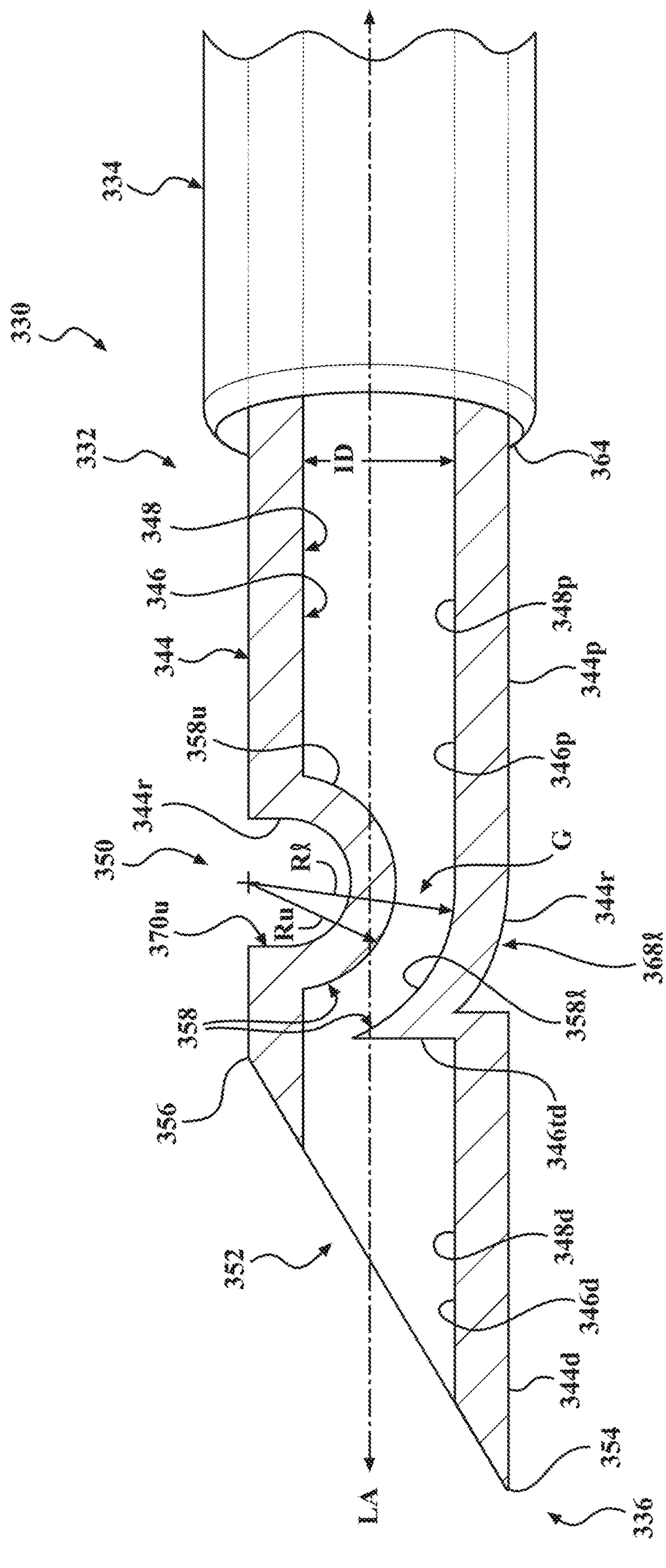
FIG. 20 is a side elevation view of a distal portion of a needle assembly in accordance with another exemplary embodiment of the present disclosure. An elongate body of the needle assembly is shown in section.
Figure 22:
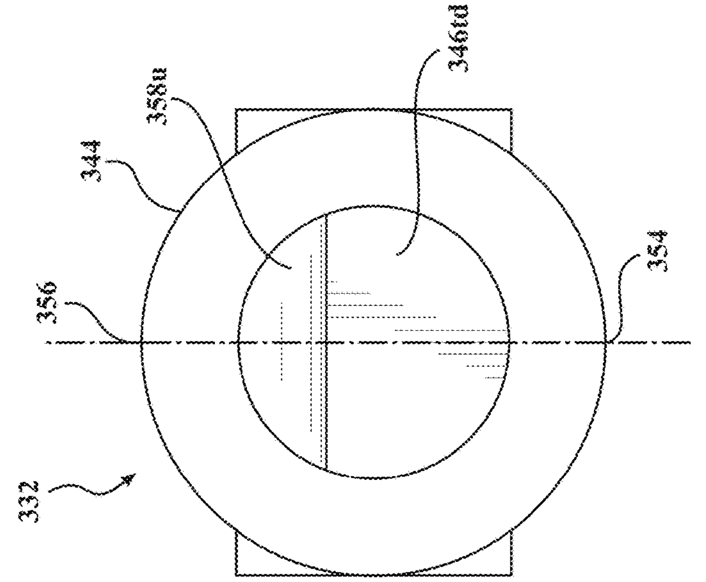
FIG. 22 is an axial view of the needle assembly of FIG. 20.
Figure 21:
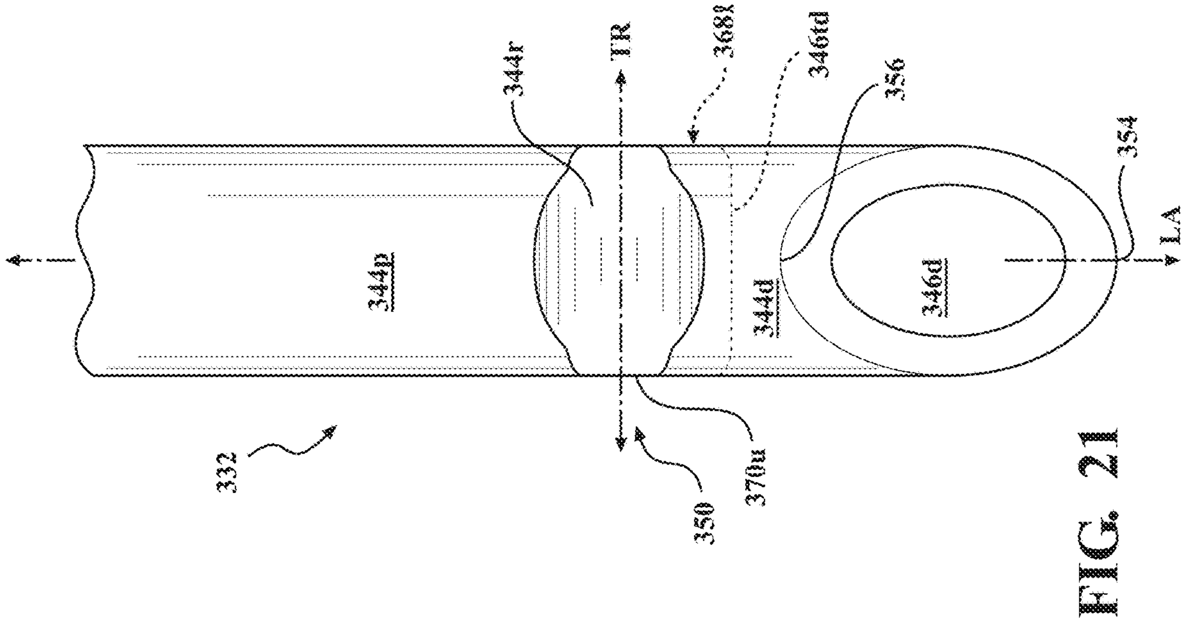
FIG. 21 is a top plan view of the needle assembly of FIG. 20.

Referring now to FIGS. 20-22, a needle assembly 330 in accordance with another exemplary embodiment is shown. In at least some respects, the needle assembly 330 of the present embodiment is the same or similar to that of FIGS. 3-19C with like numerals indicating like components plus multiples of one hundred (100). Any abbreviated or omitted description of a like-numerated component is in the interest of brevity and should not be considered absent from the present embodiment. The needle assembly 330 includes an elongate body 332, and in certain embodiments an overlying sheath 334. The elongate body 332 includes a distal end 336 and a proximal end (not shown) opposite the distal end 336 and extending distally from a hub (not shown). The elongate body 332 includes at least one sidewall 342 including an outer surface 344, and an inner surface 346 opposite the outer surface 344. The inner surface 346 defines a lumen 348 of the elongate body 332. The outer surface 344 may be associated with an outer diameter and the inner surface 346 associated with an inner diameter such that the elongate body 332 is substantially tubular in shape (other than a reverberation feature 350 to be described). A beveled tip 352 may define the distal end 336 of the elongate body 332 and include a point 354 defining an inferior aspect of the elongate body 332, and a heel 356 defining a superior aspect of the elongate body 332.

The elongate body 332 of the needle assembly 330 includes the reverberation feature 350 disposed between the distal end 336 and the proximal end. The reverberation feature 350 may include opposing portions 358 of the inner surface 346 of the sidewall 342 defining a gap (G) shaped differently than the inner surface 346 and/or sized smaller than the inner diameter (ID) of the lumen 348. The lumen 348 extending through the elongate body 332 may be defined by at least two portions, including a proximal lumen portion **348*p* defined by a proximal inner surface portion 346*p* and a distal lumen portion 348*d* defined by a distal inner surface portion 346*p*, as shown in FIG. 20. The gap (G) defined between the opposing portions 358 may axially separate and be in fluid communication with the proximal and distal lumen portions 348*p*, 348*d***.

With continued reference to FIG. 20, the inner surface 346 includes the proximal inner surface portion **346*p* defining the proximal lumen portion 348*p* that is tubular in shape. The opposing portions 358 may extend distally from the proximal inner surface portion 346*p* and extending inwardly or towards the longitudinal axis (LA) relative to the proximal inner surface portion 346*p*. In particular, the opposing portions 358 of the reverberation feature 350 may include an upper portion 358*u* at the superior aspect and a lower portion 358*l* at the inferior aspect. The upper portion 358*u* may be an arcuate surface extending towards the longitudinal axis (LA) to define the gap (G). The illustrated embodiment shows the upper portion 358*u* as a semicircular surface extending through the longitudinal axis (LA). The lower portion 358*l* may also be an arcuate surface extending distally from the proximal inner surface portion 346*p*. The arcuate surface of the lower portion 358*l* may begin at approximately a midpoint of the semicircular surface defining the upper portion 358*u*. Thus, the opposing arcuate surfaces are positioned to at least partially overlap axially along the longitudinal axis (LA). The upper portion 358*u* may include a radius of curvature $R_u$ of between 0.001 and five millimeters, and the lower portion 358*l* may include a radius of curvature $R_y$ of between 0.001 and five millimeters. The radii of curvature $R_u$, $R_l$ of the upper and lower portions 358*u*, 358*l* may be equal, and further may vary based on the dimensions of the elongate body 332 (e.g., the gauge of the needle assembly 330). The arrangement results in the gap (G) being substantially constant in size between the opposing portions 358, yet the gap (G) is smaller than and shaped differently than the lumen 348 being cylindrical in axial section. It is also contemplated that the gap (G) may vary in size in the present embodiment of the needle assembly 330**.

Extending distally from may be a distal inner surface portion **346*d*. Extending distally from the lower portion 358*l* may be a distal transition inner surface portion 346*td* (also shown in the axial view of FIG. 6). The distal transition inner surface portion 346*td* extends outwardly or away from the longitudinal axis (LA) of the elongate body 332 relative to a proximal-most aspect of the lower portion 358*l*. The distal inner surface portion 346*d* may extend distally from the distal transition inner surface portion 346*td* and the upper portion 358*u*. The distal inner surface portion 346*d* may define at least a portion of the beveled tip 352. In the illustrated embodiment, the distal transition inner surface portion 346*td* is a vertical surface defining a horizontal edge with the lower portion 358*l*. It is contemplated that the distal transition inner surface portion 346*td* may alternative be angled towards the distal end 336 to provide a smoother transition to the lower portion 358, and/or extend upwardly near the superior aspect of the elongate body 332. In certain embodiments, particularly those with the overlying sheath 334, the distal transition inner surface portion 346*td* may extend superiorly to create a distal portion of the elongate body 332** may be solid in axial section.

The outer surface 344 may be contoured to the inner surface 346 to define the sidewall 342 of substantially constant thickness. The illustrated embodiment of FIG. 20 shows the outer surface 344 including a proximal portion **344*p*, reverberation portions 344*r* corresponding to the opposing portions 358, and a distal portion 344*d*. The outer surface 344 being contoured to the inner surface 346 may result in an upper arcuate protrusion 370*u* and a lower notch 268*l*. The upper arcuate protrusion 370*u* may be defined between the upper portion 358*u* of the inner surface 346 and one of the reverberation portions 344*r* of the outer surface 344. The lower notch 368*l* may be defined between the lower portion 358*l* of the inner surface 346 and the other one of the reverberation portions 344*r* of the outer surface 344. The illustrated embodiment shows the upper arcuate protrusions 370*u* being hemicylindrical in shape and oriented transverse (TR) to the longitudinal axis (LA), as shown in FIG. 21. The lower notch 368*l* may be complementary to the upper arcuate protrusion 370*u*, and more particularly complimentarily shaped in a manner to be axially spaced apart from the upper arcuate protrusion 370*u* along the longitudinal axis (LA) to define the gap (G). The top plan view of FIG. 21 shows the contour of the outer surface 344 including the upper arcuate protrusion 370*u* and the lower notch 368*l* including the distal transition inner surface portion 346*td*** in phantom.

The reverberation feature 350 may be positioned at or near the distal end 336 of the elongate body 332, for example, immediately proximal to the beveled tip 252. Further, in embodiments including the sheath 334, the sheath 334 may include a distal end 364 axially positioned proximal to the reverberation feature 350.

Among other advantages, the needle assembly 330 of the present embodiment allows for opposing points on the opposing portions 358 to be oriented substantially perpendicular to the incident wave (*) throughout a range of angles of approach θ, in a manner of operation similar to the previously embodiment of the needle assembly 230 described with reference to FIGS. 19A-19C. In particular, owing to the axial spacing and the complementary radii of curvature $R_u$, $R_y$ of the upper and lower portions **358*u*, 358*l***, a point on each of the upper arcuate surface and the lower arcuate surface is perpendicular to the incident wave(s) (*) (and the reflected wave(s) (a, b, c, . . . )), through a range of angles of approach θ. As a result, the waves reverberate between the opposing portions 358 through the range of angles of approach θ, and visual artifact (VA) remains displayed throughout the range of angles of approach θ without needing to adjust the ultrasound device 22. The range of angles of approach θ from which the present embodiment of the needle assembly 330 is capable of reverberating the waves may be between 1 and 85 degrees, more particularly between 5 and 75 degrees, and even more particularly between 10 and 65 degrees. Such an embodiment of the needle assembly 330 may be particularly well suited with the ultrasound device 22 coupled to the anatomy of the patient, thereby freeing one of the hands of the treating medical professional for other tasks of the medical procedure.

Referring now to FIGS. 23-30, an introducer assembly 430 is shown in which an obturator 431 is removably disposed within a sheath 434. Whereas the needle assembly 30, 130, 230, 330 includes the elongate body 32, 132, 232, 332 having the lumen 48, 148, 248, 348, the obturator 431 has an elongate body 432 that is partially or entirely solid in cross section. As to be further described, the introducer assembly 430 may be positioned within the anatomy of the patient under ultrasonic guidance, after which the obturator 431 may be removed from the sheath 434 for subsequent medical tasks to be performed through the sheath 434. It should be appreciated that the sheath 434 is an optional component of the introducer assembly 430.

The elongate body 432 includes a distal end 436 opposite a proximal end 438 to define a longitudinal axis (LA) of the elongate body 432, and an outer surface 444 extends between the proximal and distal ends 436, 438. The outer surface 444 may be associated with an outer diameter such that the elongate body 432 is substantially tubular in shape. It is contemplated that, in certain variants, the elongate body 432 may be of any suitable cross-sectional shape (e.g., triangular, square, rectangular, or a higher-order polygon) and/or include a distal portion curved or angled relative to the longitudinal axis (LA). The proximal end 438 may be rigidly or removably coupled to a hub 440, and the distal end 463 may be defined by a beveled tip 452 configured to penetrate the anatomy of the patient. The beveled tip 452 may taper to an edge or point 454. Blunt or atraumatic tips are also contemplated.

The elongate body 432 of the obturator 431 includes a solid section 472. As used herein, "solid" means an axial length of the elongate body 432 that is not hollow other than the reverberation feature 450 to be described. In certain implementations, an entirety of the elongate body 432 is solid between its proximal and distal ends 436, 438. For example, the elongate body 432 may be formed from metal and unitary or monolithic in construction. In other implementations, the elongate body 432 may include a lumen along a portion of its axial length other than the solid section 472. Additionally or alternatively, an implementation to be described includes the solid section 472 being formed from a polymer within which an insert 486 that is metal is to be disposed (see FIGS. 30A-30C). Another implementation includes the solid section 472 being formed from metal, and the remaining length of the elongate body 432 formed from a polymer.

The elongate body 432 of the obturator 431 includes the reverberation feature 450 disposed within the solid section 472. As previously described in detail, the reverberation feature 450 is configured to reverberate the incident wave from the ultrasound device 22 to produce the reflected waves (see FIG. 20). The reverberation feature 450 may include a bore 474 or a cavity 476. The reverberation feature 450 may be positioned proximal or distal to the distal end 464 of the sheath 434. In implementations where the reverberation feature 450 is the bore 474 or the cavity 476, the reverberation feature 450 may be positioned distal to the distal end 464 of the sheath 434. In such an arrangement, some fluid may enter into the bore 474 or the cavity 476, which may improve reverberation of the waves. Furthermore, since it is desirable to identify the location of the distal end 436 of the needle assembly 430 as it is being advanced within the patient anatomy, the reverberation feature 450 may be positioned at or near the distal end 436 of the elongate body 432, for example, immediately proximal to the beveled tip 452. In implementations to be described, the reverberation feature 450 may be integrated with the beveled tip 452. It is further appreciated that the reverberation feature 450 may be positioned at any suitable location between the proximal and distal ends 436, 438 of the elongate body 432.

Figure 23:
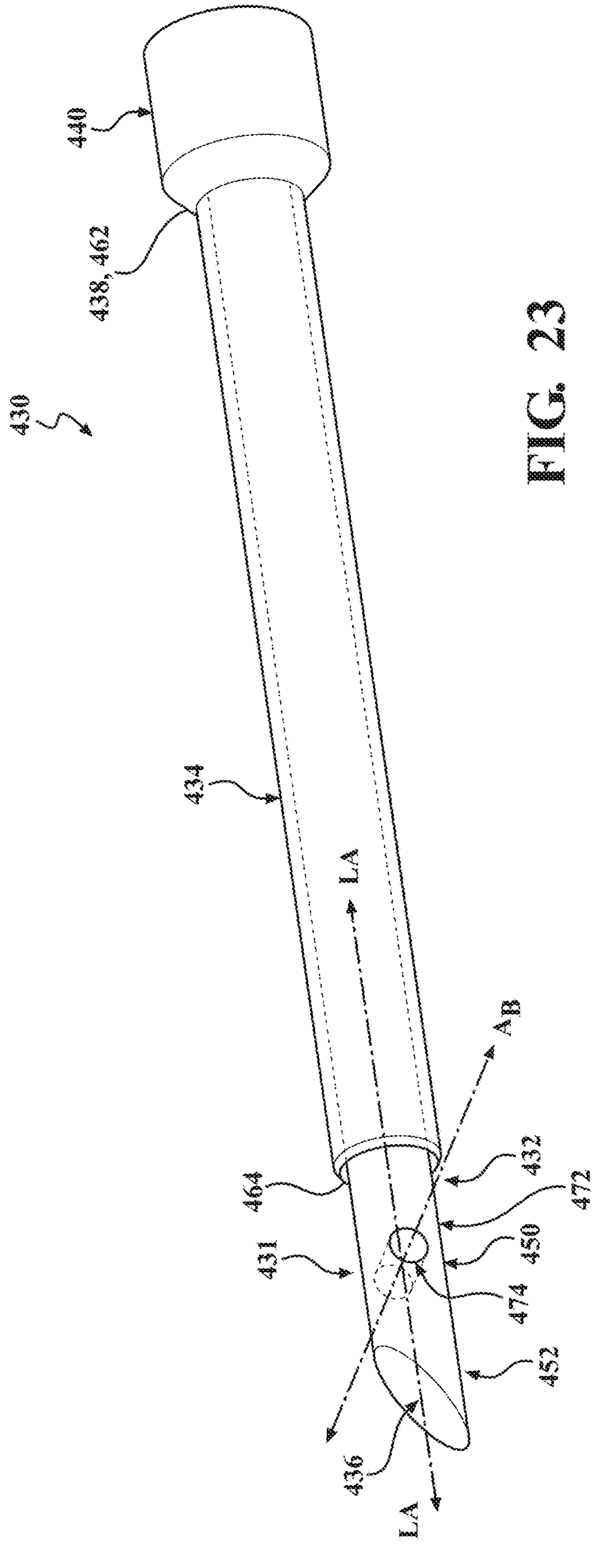
FIG. 23 is a side perspective view of an introducer assembly in accordance with an exemplary embodiment of the present disclosure in which a reverberation feature includes a bore extends through an obturator. The obturator is removably disposed within a sheath.

FIG. 23 shows one implementation of the reverberation feature 450 in which the bore 474 extends through the solid section 472, more particularly through an entirety of the solid section 472 between opposing sides of the outer surface 444. In implementations where the bore 474 does not extend through an entirety of the solid section 472, the reverberation feature 450 may be considered the cavity 476 (see FIG. 27A or 27B). As mentioned, the bore 474 or the cavity 476 may be sized to permit ingress of fluid when the introducer assembly 430 is deployed. For example, blood or other bodily fluids from adjacent tissue structures may flow within the bore 474 as the obturator 431 is advanced within the tissue. Owing to a surface 478 defining the bore 474 or the cavity 476 being metal—i.e., reflective of ultrasonic waves—and/or the bore 474 or the cavity 476 being filled with the fluid—i.e., reflective or refractive of ultrasonic waves—the waves may be altered during reverberation within the reverberation feature 450. The altering of the waves in speed and/or direction is associated with latency or irregularity in return time reaching the ultrasound device 22, and the visual artifact is generated by the ultrasound system 24 based on the latency or return time.

The bore 474 is angled relative the longitudinal axis (LA). In other words, the bore axis ($A_B$) is not parallel or collinear with the longitudinal axis (LA). The bore 474 may be angled within the range of approximately 20 degrees to 160 degrees, or more particularly within the range of approximately 50 to 130 degrees, or even more particularly within the range of approximately 80 to 100 degrees. FIG. 23 shows the bore axis ($A_B$) being transverse or at a right angle relative to the longitudinal axis (LA). For example, with the bore 474 being transverse to the longitudinal axis (LA), a portion of the surface 478 defining the bore 474 is generally perpendicular to the incident wave from the ultrasound device 22 at most or all angles of approach θ. Over known needle assemblies having in which a portion a smooth tubular longitudinal lumen may only be perpendicular to the incident wave when the angle of approach is zero (rarely feasible in practice), the bore 474 is perpendicular to the waves over a range of angles of approach θ utilized in most to all medical procedures.

Figure 24:
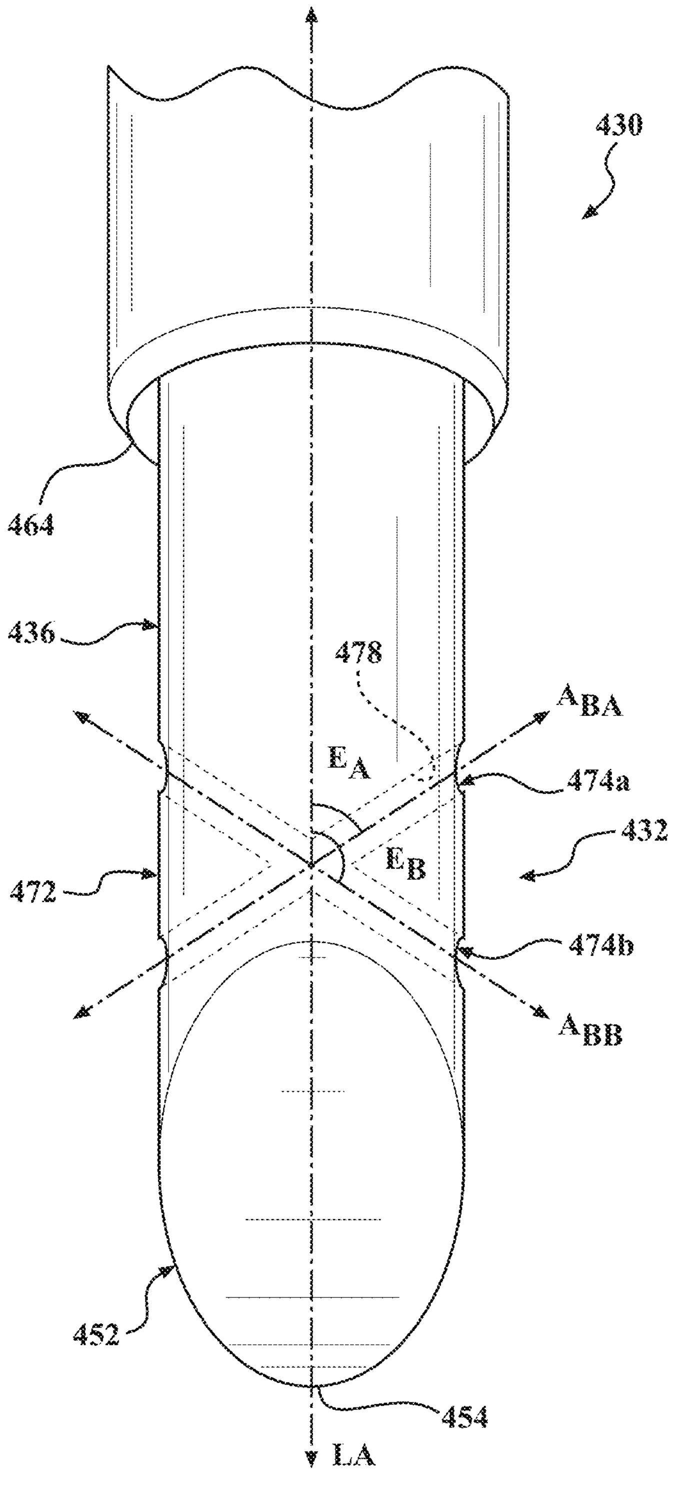
FIG. 24 is a top plan view of an introducer assembly in which bores extend through the obturator and are angled relative to a longitudinal axis of the obturator.

In another implementation, FIG. 24 shows the reverberation feature 450 including a first bore **474*a*, and a second bore 474*b* intersecting with the first bore 474*a*. The first bore 474*a* is angled relative to the longitudinal axis (LA) at an angle $E_A$, and the second bore 474*b* is angled relative to the longitudinal axis (LA) at an angle $E_B$. The angles may be the same or different. The illustrated arrangement represents that non-transverse orientations of the bore 474 are contemplated. Further, FIGS. 23 and 24 show the bore(s) generally oriented laterally (when the introducer assembly 430 is oriented for deployment), and it is contemplated that the bore(s) 474 may be arranged in any suitable radial orientation. For example, the bores(s) 474 may be vertically oriented (see, e.g., a third bore 474*c* of FIG. 25). For another example, the bore(s) 474 may be radially clocked relative to the bore axis ($A_B$) of FIG. 23**.

Figure 25:
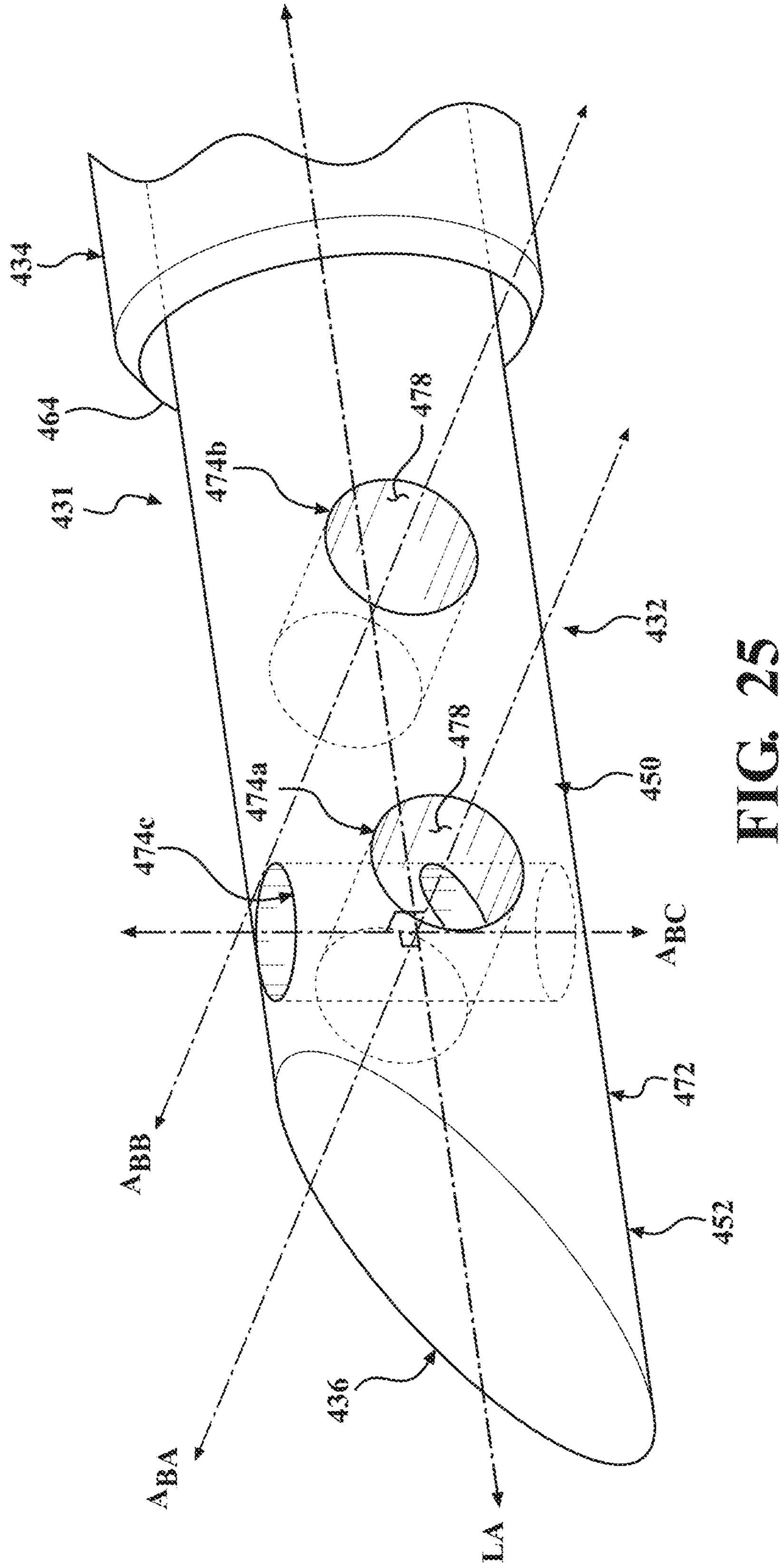
FIG. 25 is a side perspective view of a distal portion of an introducer assembly in which more than one bore extend through the obturator.
Figure 26A:
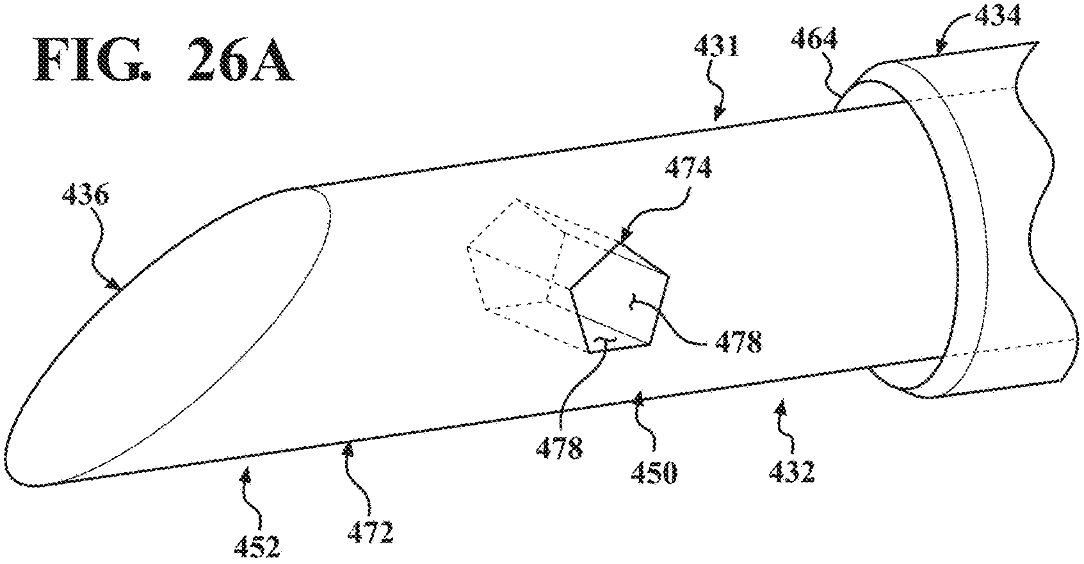
FIGS. 26A-26E are side perspective views of a distal portion of an introducer assembly in which a shape of the bore may be varied. Various alternatives for the shape are also provided.
Figure 26B:
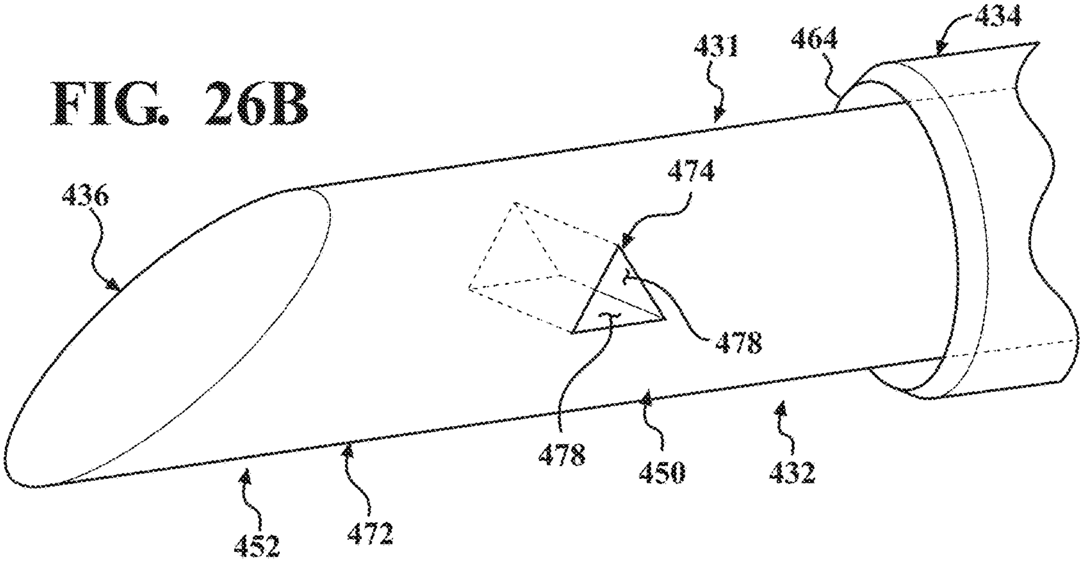
Figure 26C:
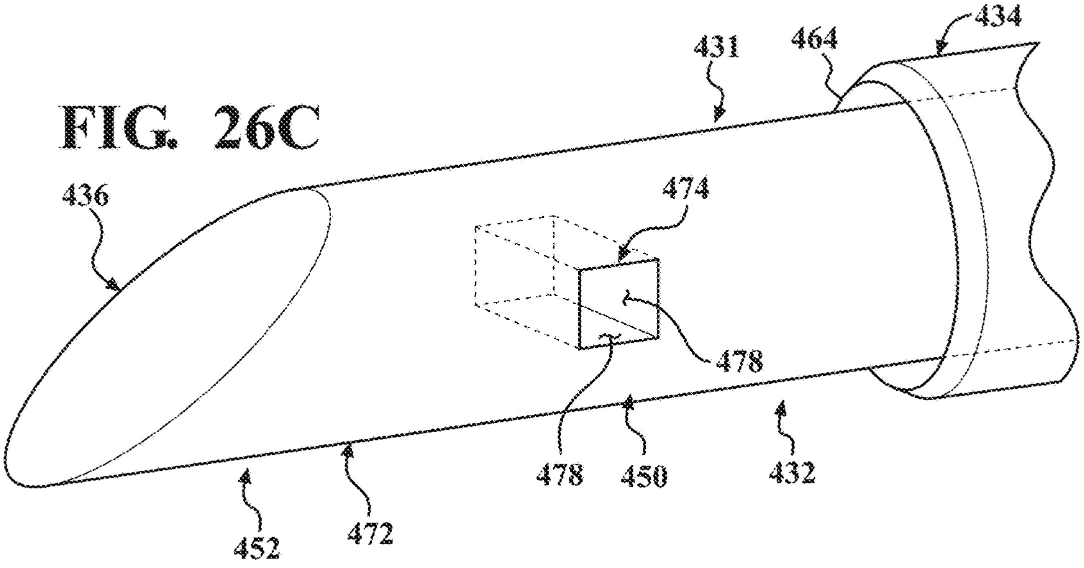
Figure 26D:
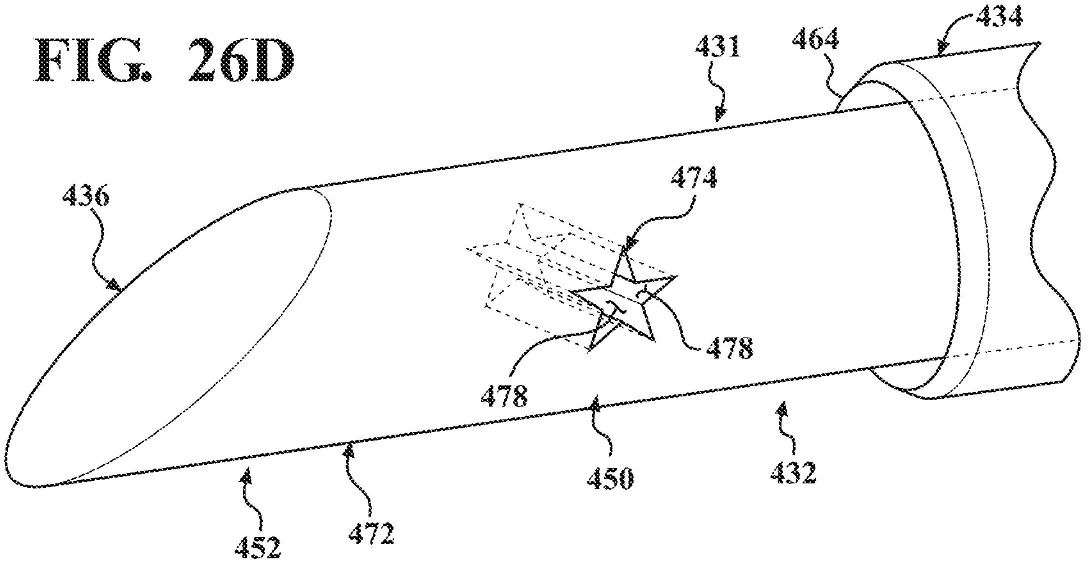
Figure 26E:
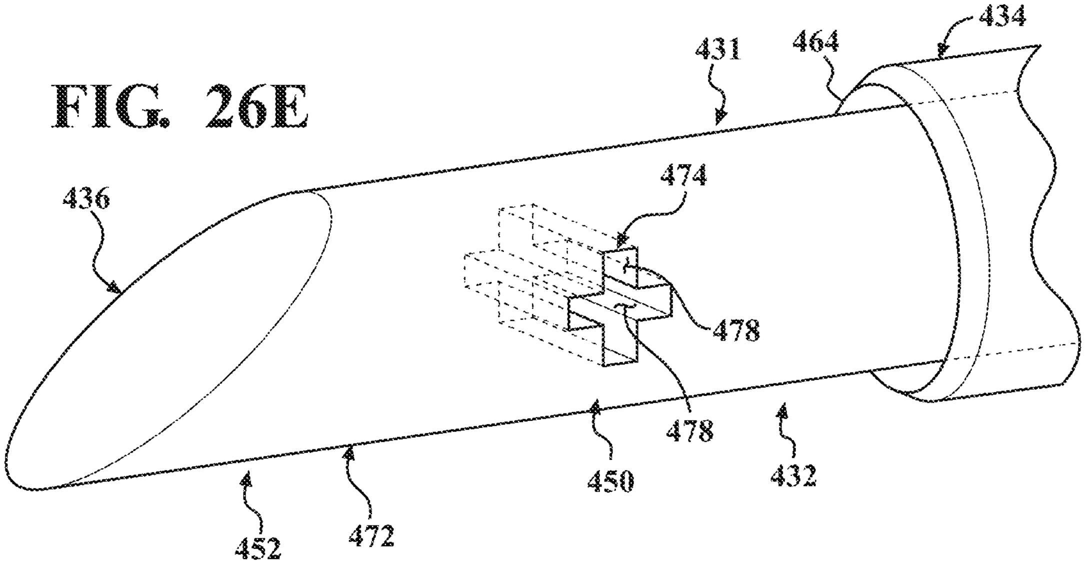

The bore 474 may be a singular bore, which may be advantageous from at least a manufacturing perspective. In other implementations, more than one bore 474 may be provided. As previously introduced, FIG. 24 shows the first and second bores 474*a*, 474*b* that intersect and are each angled relative to the longitudinal axis (LA). More particularly, the first bore 474*a* is radially oriented laterally and has a first bore axis ($A_{BA}$) angled relative to the longitudinal axis (LA), and the second bore 474*b* is radially oriented laterally and has a second bore axis ($A_{BB}$) angled relative to the longitudinal axis (LA) and the first bore axis ($A_{BA}$). Referring now to FIG. 25, the reverberation feature 450 may include the three bores, namely the first bore 474*a*, the second bore 474*b*, and a third bore 474*c*. The first and second bores 474*a*, 474*b* are parallel to one another and spaced apart axially along the longitudinal axis (LA). More particularly, the first bore axis ($A_{BA}$) and the second bore axis ($A_{BB}$) are parallel to one another, and the first bore axis ($A_{BA}$) and the second bore axis ($A_{BB}$) may be transverse to the longitudinal axis (LA). It is understood that the reverberation feature 450 may include three, four, or five or more bores spaced apart axially along the longitudinal axis (LA). The third bore 474*c* is radially oriented vertically and intersects with the first bore 474*a*. A third bore axis ($A_{BC}$) is shown as being perpendicular to the first bore axis ($A_{BA}$) and the longitudinal axis (LA). The intersection of the bores 474 results in area of the surfaces 478 defining the bores 474 and unique geometries that may improve reverberation of the reflected waves, particularly at a greater range of angles of approach θ. It should be appreciated the bores 474 may or may not intersect.

As mentioned, the reverberation feature 450 may be a singular bore, and FIG. 23 shows the singular bore being tubular in shape (i.e., circular in section). FIGS. 26A-E illustrate that other shapes of the bore 474 are contemplated in which increased area of the surface(s) 478 defining the bore 474 and unique geometries may improve reverberation of the reflected waves. The bore 474 may be a pentagonal, triangular, square, stellate, or cruciform, among others. Additional higher-order polygons are shapes are contemplated. In implementations with more than one bore 474, the bores 474 may have the same shape or be differently shaped. It should also be appreciated that the shape of the bore 474 may be combined with other features of the bore(s) 474 described throughout the present disclosure (e.g., angle, radial orientation, plug 480, insert 486, etc.).

Figure 27A:
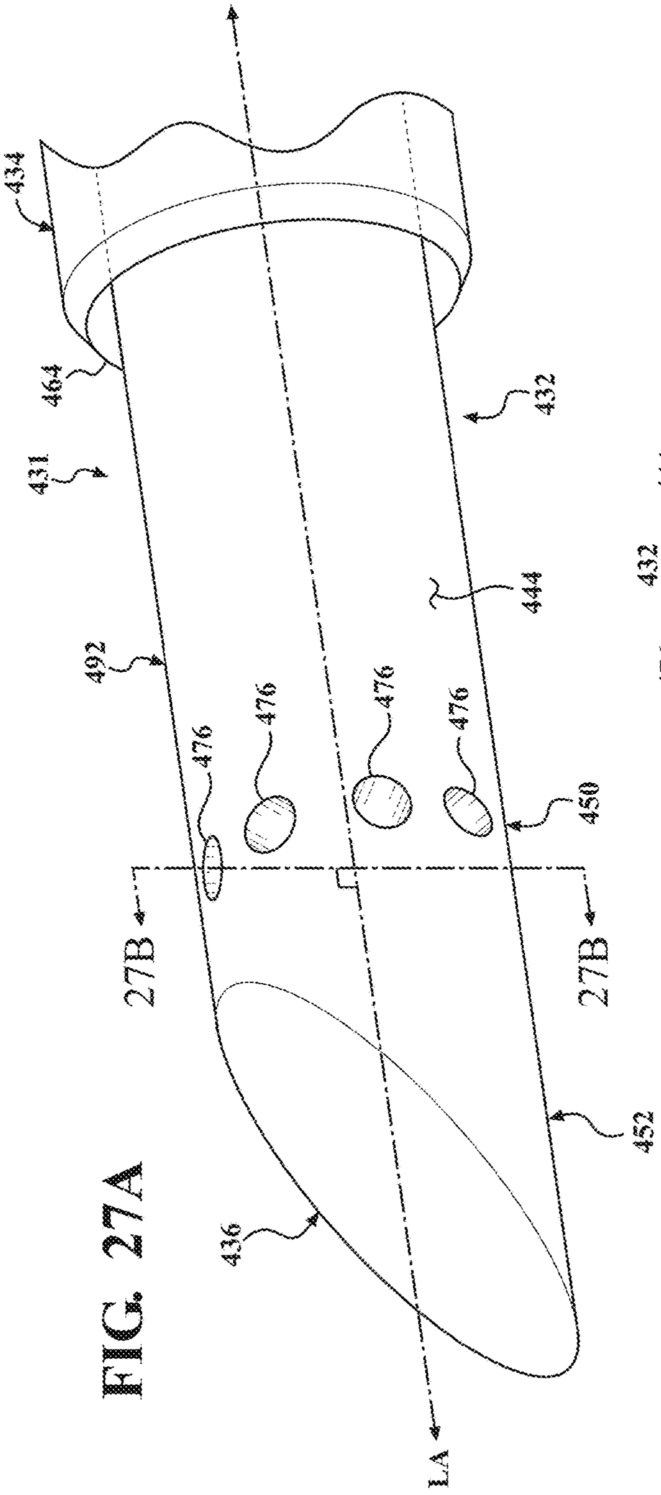
FIG. 27A is a side perspective view of a distal portion of an introducer assembly in which cavities are disposed through the obturator.
Figure 27B:
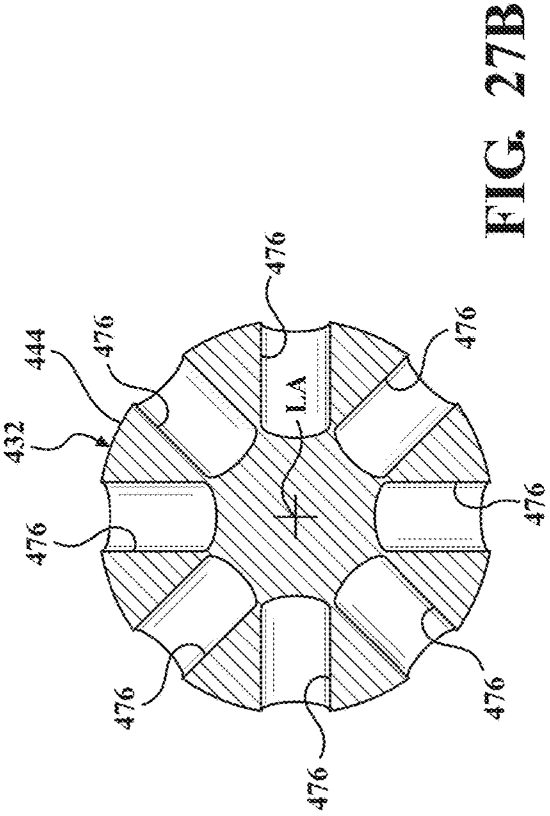
FIG. 27B is an axial section view of the introducer assembly of FIG. 27A taken along lines 27B-27B.

Whereas the bore 474 extends through the solid section 472, in other implementations, at least one cavity 476 is disposed within the solid section 472. The cavity 476 may not extend through opposing sides of the outer surface 444. In other words, the cavity 476 extends from the outer surface 444 by a portion of the width of the elongate body 432. Referring now to FIGS. 27A and 27B, an exemplary implementation is shown in which cavities 476 are disposed within the solid section 472 and arrange radially about the outer surface 444. The cavities 476 may be equiangularly spaced radially and axially located at a common position along the elongate body 432, as shown in FIG. 27A. In other implementations, a second, third or four or more ring-like arrangements of the cavities 476 may be provided. Alternatively, the cavities 476 may be arranged randomly radially and/or axially about and along the longitudinal axis (LA), respectively. It is not necessary that there be multiple cavities 476, but rather a singular cavity 476 may be provided at any suitable location within the solid section 472.

The cavities 476 may extend from the outer surface 444 towards the longitudinal axis (LA), and the cavities 476 may be oriented perpendicular to the longitudinal axis (LA). In other implementations, the cavities 476 may be oriented in any suitable orientation—radially and/or axially—and each of the cavities 476 may be oriented the same or differently. It should also be appreciated that the cavity 476 or cavities 476 may be combined with other features described throughout the present disclosure (e.g., shape, plug 480, insert 486, etc.).

Figure 28:
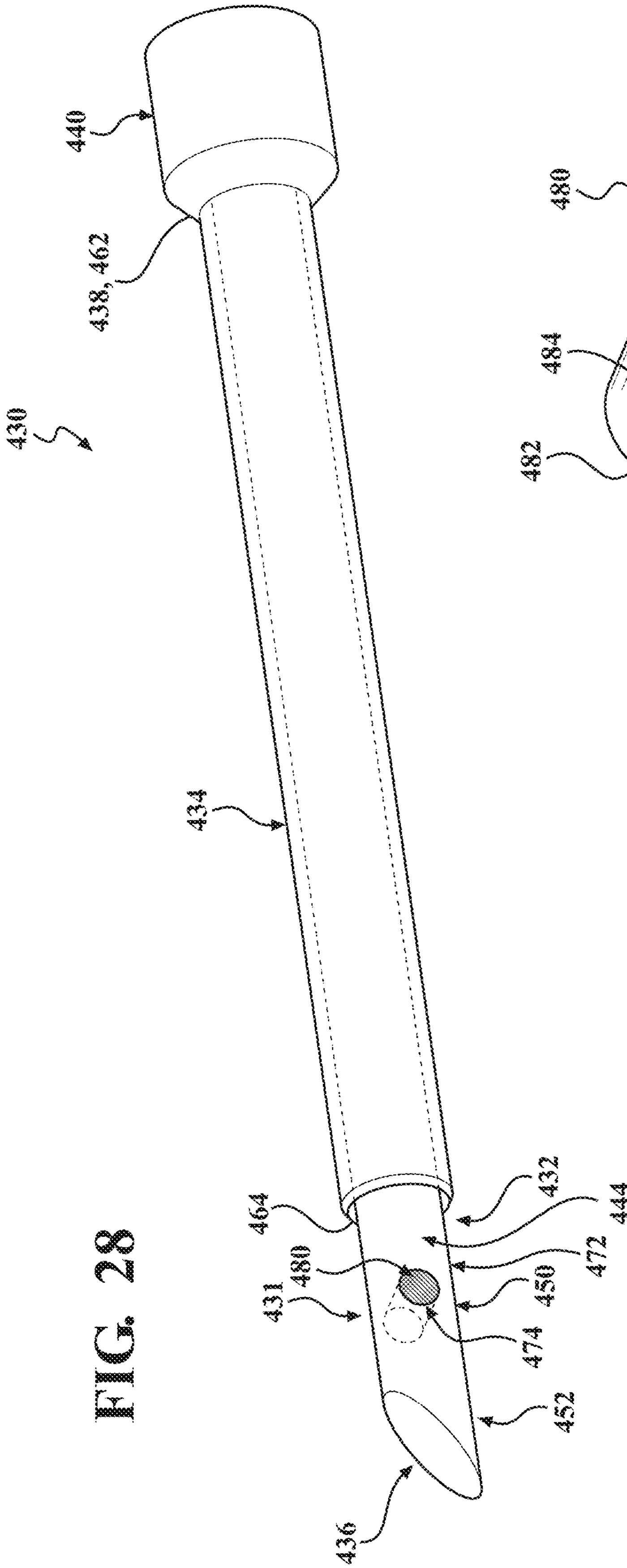
FIG. 28 is a side perspective view of a distal portion of an introducer assembly in which a plug is disposed within the bore.
Figure 29:
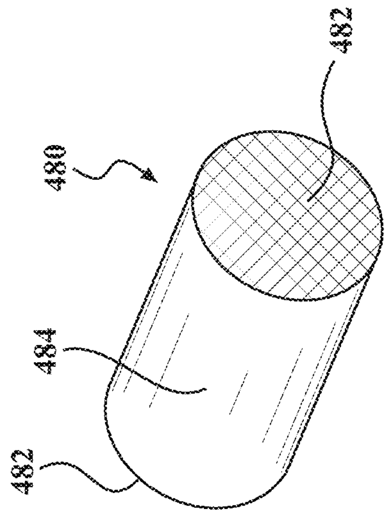
FIG. 29 is a perspective view of a representation of the plug of FIG. 28.

Referring now to FIGS. 28 and 29, the introducer assembly 430 is shown in which the bore 474 is positioned distal to the distal end 464 of the sheath 434. A plug 480 is disposed within the bore 474. The plug 480 is sized and shaped complementary to the size and shape of the bore 474. For example, the plug 480 may be cylindrical in shape and include opposing ends 482 and at least one outer surface 484 extending between the ends 482. In other examples, the plug 480 may be pentagonal, triangular, square, stellate, cruciform, or the like. The plug 480 may be generally solid and/or uniform in section. With the plug 480 disposed within the bore 474, the ends 482 of the plug 480 may be flush with the outer surface 444 of the elongate body 432. An adhesive may be used to secure the plug 480 within the bore 474, or alternatively the plug 480 may be friction fit within the bore 474. In implementations in which there are more than one bore 474, more than one plug 480 may be provided. It is also understood that the plug 480 may also be used with implementations with one or more cavities 476.

The plug 480 may be configured to alter the density of the medium through which the waves are traveling. The plug 480 may alter the speed of the reflected waves, and/or the plug 480 may be configured to refract or scatter the reflected waves. The altering of the waves, among other characteristics, may result in latency or irregularity in return time of the reflected waves, thereby producing or improving the visual artifact (VA) generated by the ultrasound system 24. To that end, the plug 480 may be formed from a material different than the material forming the elongate body 432, and/or the plug 480 may include external or internal geometries. For example, the solid section 472 of the elongate body 432 may be formed from metal, and the plug 480 may be a sorbent such as a foam or a sponge. The sorbent may absorb bodily fluids as the introducer assembly 430 is deployed within the anatomy of the patient. The fluid-filled sorbent enhances reflectivity or refractivity of the ultrasonic waves for reasons discussed below, thereby further altering the waves during reverberation within the reverberation feature 450. Alternatively, the sorbent may be impregnated with a fluid such as water, saline, or gel prior to deployment within the anatomy of the patient. In other implementations, the plug 480 may be formed from an elastomer such as silicone, a polymer, or the like. In other implementations, the plug 480 formed from a material including interstices or microbubbles, and/or the plug 480 may be a fluid-filled chamber.

The aforementioned implementations utilizing fluid with the reverberation feature 450 may be configured to mimic B-lines often produced during ultrasound observation of the lungs. Typically, air predominates the lungs such that sufficient acoustic conditions are not present for B-lines; however, in certain instances, fluid-rich interstitia (i.e., bubble-tetrahedral complexes) may result in visual artifacts. The introducer assembly 430 including the microbubbles or fluid-filled sorbent of the plug 480 and/or fluid within the bore 474 may mimic such complexes and, when struck by the incident wave and/or reflected waves, may result in signals being persistently emitted back to the ultrasound device 22. In response, the ultrasound system 24 generates the visual artifact (VA) described throughout the present disclosure that is especially well pronounced.

Figure 30A:
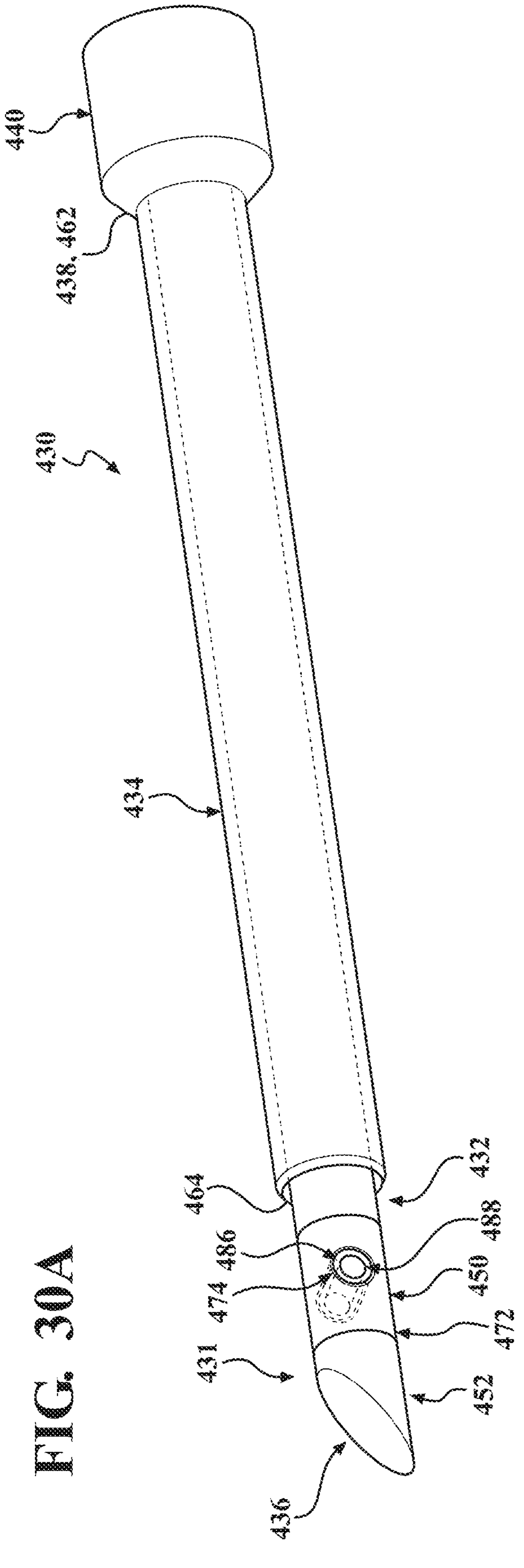
FIGS. 30A-30C are side perspective views of a distal portion of an introducer assembly in which an insert is disposed within a bore.
Figure 30B:
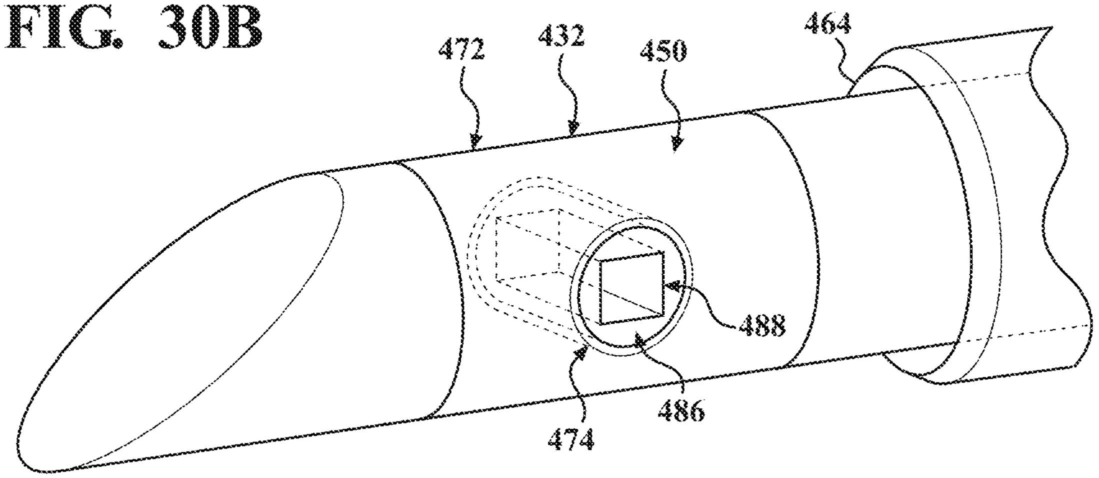
Figure 30C:
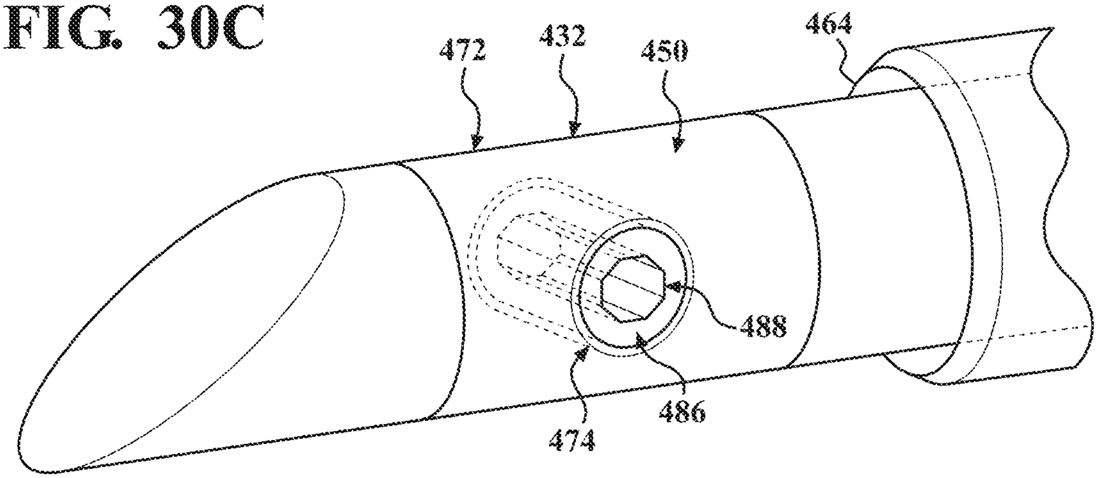

FIGS. 30A-30C shows the introducer assembly 430 is shown in which the solid section 472 is discrete from at least one of a proximal length of the elongate body 432 and the beveled tip 452. The solid section 472 may be joined to the proximal length and the beveled tip 452 through known manufacturing techniques. The solid section 472 may be formed from a polymer, whereas the proximal length of the elongate body 432 and/or the beveled tip 452 is formed from a metal. An insert 486 may be disposed within the bore 474 and configured to alter the speed of the reflected waves for reasons previously explained. Whereas the plug 480 previously described was solid in section, the insert 486 may define an insert bore 488.

The insert 486 may be formed from a material different than the material forming the solid section 472. For example, in implementations where the solid section 472 is formed from a polymer, the insert 486 may be formed from a metal. Thus, reflectivity or refractivity of the ultrasonic waves may occur at an interface between the bore 474 and an outer surface of the insert 486, and reverberation may further occur within the insert bore 488. The insert bore 488 may be tubular in shape such that the insert 486 is ring-like in shape, as shown in FIG. 30A, or the insert bore 488 may be square or octagonal as shown in FIGS. 30B and 30C, respectively. Other shapes are also contemplated like those introduced for the bore 474, e.g., pentagonal, triangular, square, stellate, and cruciform. The shape of the insert bore 488 may be the same or different than the shape of the bore 474 within which the insert 486 is disposed. FIGS. 30B and 30C show examples of the shape of the insert bore 488 being different than the shape of the bore 474. A plug (not shown), akin to those previously described, may be disposed within the insert bore 488 of the insert 486. For example, the plug within the insert 486 may be formed from a sorbent. In such an example, reflectivity or refractivity of the ultrasonic waves may occur at an interface between the bore 474 and the insert 486, at an interface between the insert 486 and the plug, and within the plug with fluid absorbed within the sorbent.

Referring now to FIGS. 31A-32B, the introducer assembly 530 is shown in which the reverberation feature 550 is integrated with the beveled tip 552. In at least some respects, the introducer assembly 530 of the present embodiment is the similar to that of FIGS. 23-30 with like numerals indicating like components plus one hundred (100). Any abbreviated or omitted description of a like-numerated component is in the interest of brevity and should not be considered absent from the present embodiment. The elongate body 432 includes the distal end 436 opposite the proximal end 538 to define a longitudinal axis (LA) of the elongate body 532, and an outer surface 544 extending between the proximal and distal ends 536, 538. The proximal end 538 may be rigidly or removably coupled to a hub 540, and the distal end 563 may be defined by the beveled tip 552. As mentioned, the elongate body 532 of the obturator 531 includes the solid section 572, and in the embodiment of FIGS. 31A-32B, the beveled tip 552 may be considered the solid section 572. In this instance, "solid" means the beveled tip 552 is not hollow other than the reverberation feature 550.

Figure 31A:
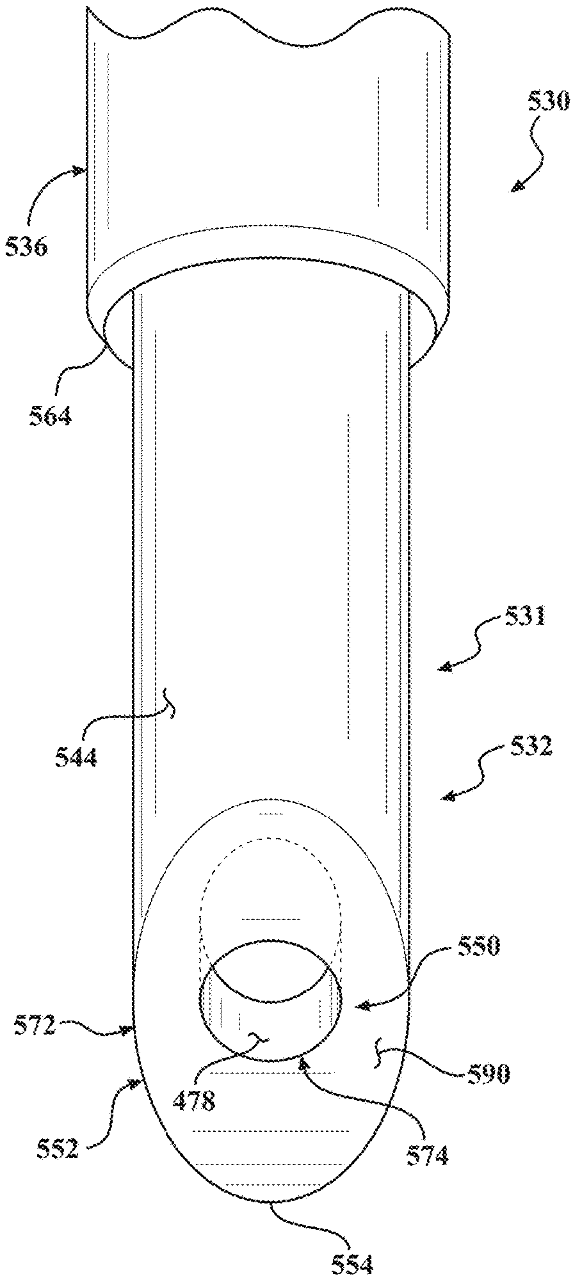
FIG. 31A is a top plan view of a distal portion of an introducer assembly in which a bore extends through a beveled tip of the obturator.
Figure 31B:
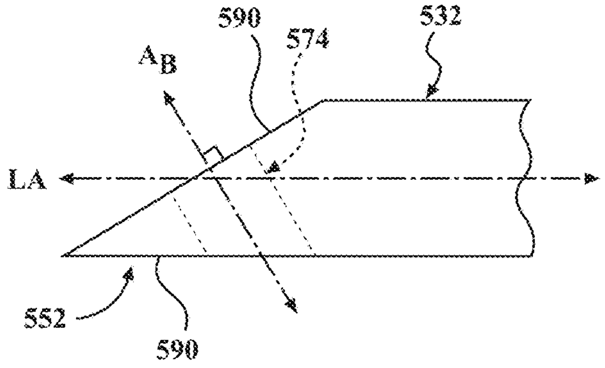
FIGS. 31B and 31C are side elevation views of the distal portion of the introducer assembly showing exemplary orientations in which the bore may extend through the beveled tip.
Figure 31C:
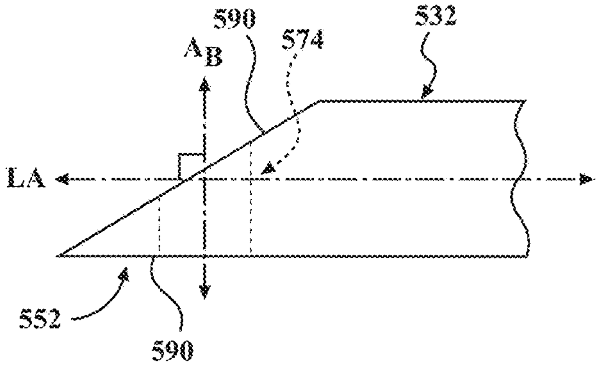

The elongate body 532 of the obturator 531 includes the reverberation feature 550 disposed within the solid section 572, in particular the beveled tip 552. Referring to FIG. 31A-31C, the beveled tip 552 includes surfaces 590 (one shown) tapering to an edge or point 554. The bore 574 may extend through the beveled tip 552 between the surfaces 590. As a result, the bore 574 is generally oriented vertically when the introducer assembly 530 is oriented for deployment. The bore axis ($A_B$) of the bore 574 may be oriented perpendicular to an upper one of the surfaces 590, as shown in FIG. 31B, such that the bore 574 is angled relative to the longitudinal axis (LA). Alternatively, the bore axis ($A_B$) of the bore 574 may be oriented perpendicular to the longitudinal axis (LA), as shown in FIG. 31C. Other suitable angles between the bore axis ($A_B$) and the longitudinal axis (LA) are contemplated, which may be based, at least in part, on anticipated angles of approach $\theta$ of the introducer assembly 530.

Figure 32A:
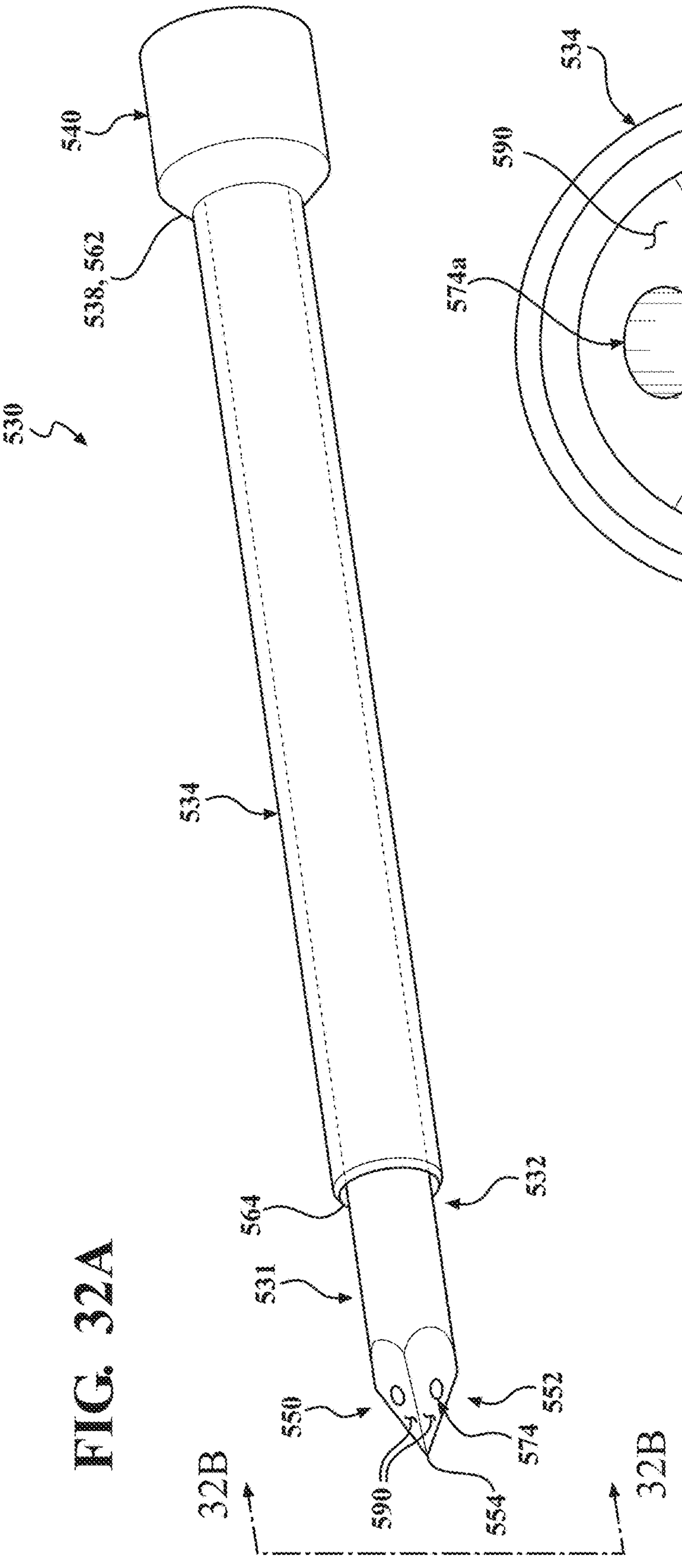
FIG. 32A is a side perspective view of a distal portion of an introducer assembly in which bores extend through surfaces of the beveled tip.
Figure 32B:
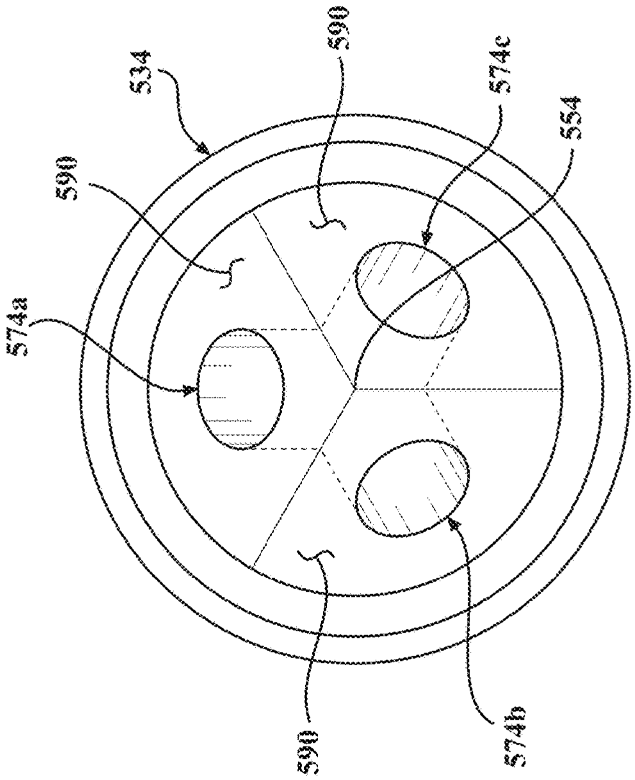
FIG. 32B is an axial view of the beveled tip of FIG. 32A taken along lines 32B-32B.

FIGS. 32A and 32B shows the beveled tip 552 including three surfaces 590 tapering to the point 554. Each of three bores 574*a*, 574*b*, 574*c* extends through a respective one of the surfaces 590. The bores 574*a*, 574*b*, 574*c* intersect within the beveled tip 552. As generally appreciated from FIG. 32B, the bores 574*a*, 574*b*, 574*c* are equiangularly spaced radially. Other radial arrangements are contemplated based on a number of surfaces 590 of the beveled tip 552 and a number of the bores 574.

In certain implementations, the cavities 476 previously described may be disposed within the surfaces 590 of the beveled tip 552 as opposed to the bores 574*a*, 574*b*, 574*c*. Further, the features associated with the plug 480 and the insert 486 may be included on implementations in which the reverberation feature 550 is integrated with the beveled tip 552.

Operation of the reverberation feature 450, 550 similar in at least some respects to the reverberation feature 50, 150, 250, 350 described with reference to FIGS. 7-10. In particular, once the incident wave encounters the reverberation feature 450, 450, the waves reverberate, for example, within the bore(s) 474, 574. The reverberated waves are received by the ultrasound system as echoes with the echoes being reproduced on the display as the visual artifact (VA), for example, a series of bright pixels, that may have the appearance of a straight vertical line. Based on the proximity between the reverberation feature 450, 550 and the distal end 436, 536, and the continuous imaging provided by a display 26 of the ultrasound system 24, visual guidance is provided to the treating medical professional as she or he locates the distal end 436, 536 of the introducer assembly 430, 530 at the target anatomy.

The obturator 431, 531 may be removed from within the sheath 434, 534 with the sheath 434, 534 remaining positioned near and providing access to the target anatomy. Subsequent medical tasks may be performed through the sheath 434, 534. For example, a biopsy device may be directed through the sheath 434, 534 with an operable feature of the biopsy device positioned beyond the sheath 434, 534 and at the target anatomy. The biopsy device may be actuated to obtain a tissue sample. For another example, other instrumentation may be directed through the sheath to perform various medical tasks such as resection, ablation, or the like.

Figure 33A:
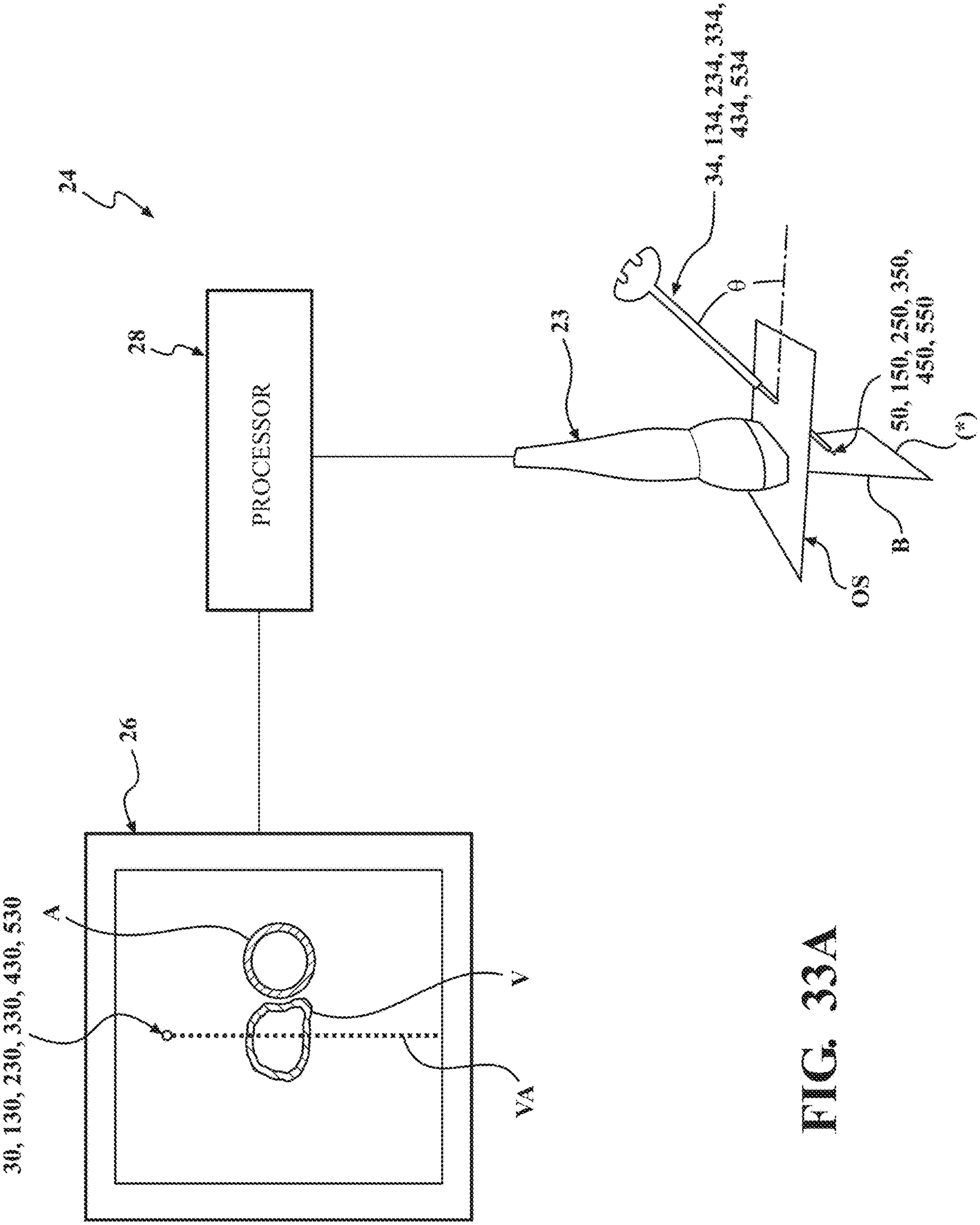
FIG. 33A is a schematic diagram of an ultrasound system for facilitating visual guidance with the assemblies of the present disclosure. The "out of plane" technique is being utilized to view the needle in cross section with cross sections of a vein (V) and an artery (A).
Figure 33B:
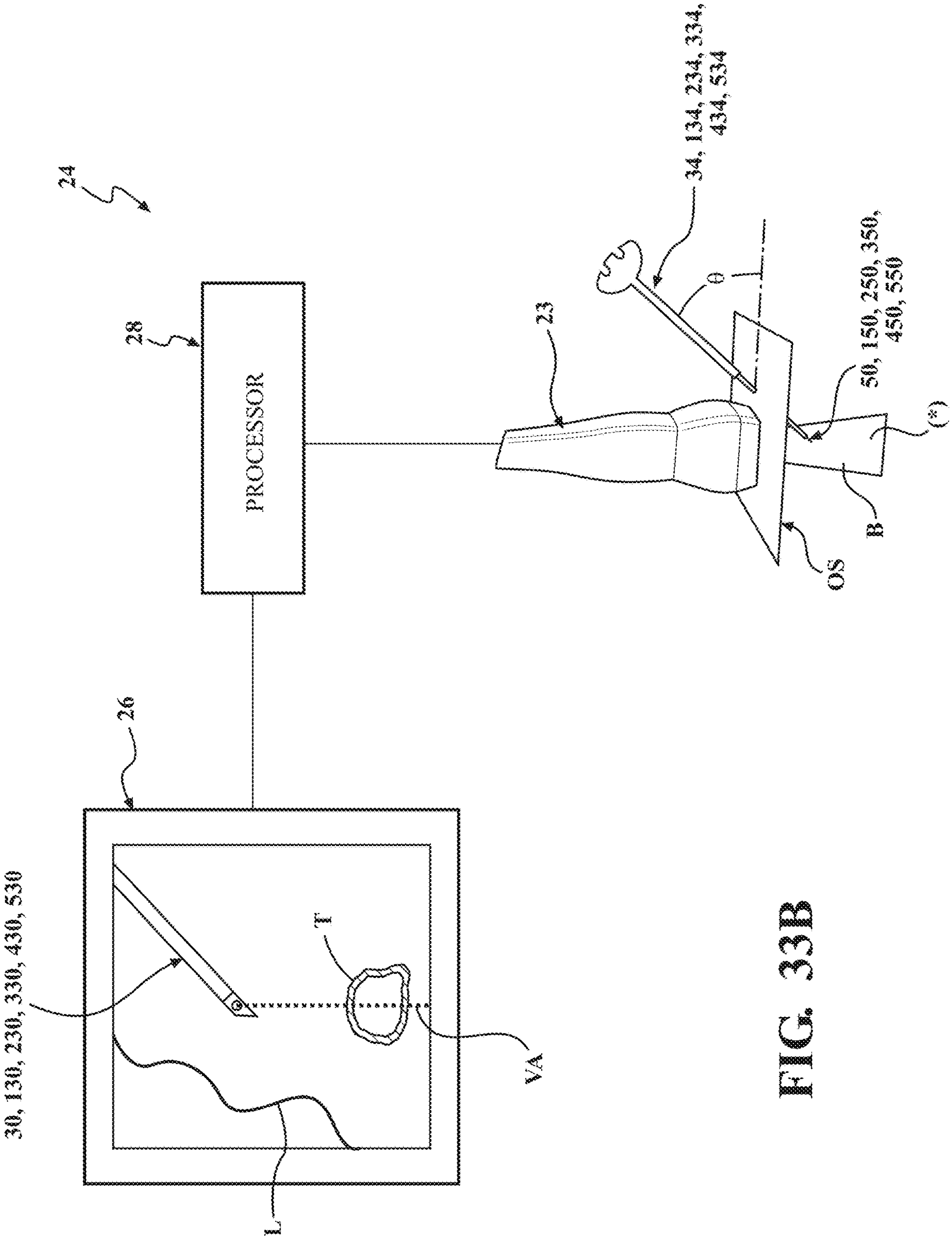
FIG. 33B is a schematic diagram of the ultrasound system for facilitating visual guidance with the assemblies of the present disclosure. The "in plane" technique is being utilized to position the assembly at target anatomy for biopsy.

Referring now to FIGS. 33A and 33B, a method of positioning the assembly 30, 130, 230, 330, 430, 530 within a target anatomy of a patient under visual guidance from an ultrasound system 24 is described. The ultrasound system 24 includes the ultrasound device 22, for example a probe 23 capable of being manipulated by the treating medical professional. The ultrasound system 24 also includes a display 26 in electronic communication with the probe 23. A processor 28 may be in electronic communication with the probe 23 and the display 26 and configured to receive and process signals from the probe 23 and transmit display signals to the display 26. The assembly 30, 130, 230, 330, 430, 530 may be any one of the aforementioned embodiments. The assembly 30, 130, 230, 330, 430, 530 includes the elongate body 32, 132, 232, 332, the beveled tip 52, 152, 252, 352, 452, 552, and the reverberation feature 50, 150, 250, 350, 450, 550. The reverberation feature 50, 150, 250, 350 may include the opposing portions 58, 158, 258, 358 of the inner surface 46, 146, 246, 346 defining the gap (G) shaped differently than the inner surface 46, 146, 246, 346, or the reverberation feature 450, 550 may include the bore 474, 574 or the cavity 476, 576 disposed within the solid section 472, 572 of the elongate body 432, 532.

Referring to FIG. 33A, the beveled tip 52, 152, 252, 352, 452, 552 may be penetrated through the overlying skin surface (OS) to direct the assembly 30, 130, 230, 330, 430, 530 towards the target anatomy, for example a vessel such as a vein (V) or artery (A). The assembly 30, 130, 230, 330, 430, 530 is directed towards the target anatomy at an angle of approach θ relative to the overlying skin surface (OS). The probe 23 is positioned external to the overlying skin surface (OS) at a location above the target anatomy. For accessing the vessel, the "out of plane" technique may be particularly advantageous. The probe 23 is operated to direct an incident wave (*) (see FIGS. 7, 14 and 19A-19C) through the overlying skin surface (OS) and towards the target anatomy. The assembly 30, 130, 230, 330, 430, 530 and/or the probe 23 is manipulated such that the incident wave is reverberated with the reverberation feature 50, 150, 250, 350, 450, 550 to generate reflected waves (a, b, c, . . . (see FIGS. 7, 14 and 19A-19C)). For example, the assembly 30, 130, 230, 330, 430, 530 and/or the probe 23 may be manipulated to substantially align the reverberation feature 50, 150, 250, 350, 450, 550 with the incident wave (*). Further, the assembly 30, 130, 230, 330, 430, 530 and/or the probe 23 may be manipulated to alter the angle of approach θ to align the reverberation feature 50, 150, 250, 350, 450, 550. The method may include viewing on the display 26 the visual artifact (VA) generated with the ultrasound system 24 based on the reflected waves (a, b, c, . . . ). For example, assembly 30, 130, 230, 330, 430, 530 and/or the probe 23 may be manipulated to cause the visual artifact (VA) to intersect a cross section of the vessel, for example the vein (V (see FIG. 20). The assembly 30, 130, 230, 330, 430, 530 may be manipulated to cause the beveled tip 52, 152, 252, 352, 452, 552 and the distal end 64, 164, 264, 364 of the sheath 34, 134, 234, 334 to penetrate the vessel. Based on the visual artifact (VA) displayed on the display 26 and generated by the reverberation feature 50, 150, 250, 350, 450, 550 reverberating the waves, placement of the assembly 30, 130, 230, 330, 430, 530 (including the distal end 64, 164, 264, 364, 464, 564 of the sheath 34, 134, 234, 334, 434, 534) may be confirmed. Thereafter, the elongate body 32, 132, 232, 332 of the assembly 30, 130, 230, 330, 430, 530 may be removed from within the vessel and the sheath 34, 134, 234, 334, 434, 534 while leaving the distal end 64, 164, 264, 364, 464, 564 of the sheath 34, 134, 234, 334, 434, 534 within the vessel. Any number of medical tasks may be performed using the sheath 34, 134, 234, 334, 434, 534 providing a conduit to an interior of the vessel, for example, blood sampling and/or therapy delivery.

Referring now to FIG. 33B, the beveled tip 52, 152, 252, 352, 452, 552 may be penetrated through the overlying skin surface (OS) to direct the assembly 30, 130, 230, 330, 430, 530 towards the target anatomy, for example a tumor (T) within the lung (L). The assembly 30, 130, 230, 330, 430, 530 is directed towards the target anatomy at an angle of approach θ relative to the overlying skin surface (OS). The probe 23 is positioned external to the overlying skin surface (OS) at a location above the target anatomy. For locating the beveled tip 52, 152, 252, 352, 452, 552 within soft tissue for biopsy, the "in plane" technique may be particularly advantageous. The probe 23 is operated to direct the incident wave (*) through the overlying skin surface (OS) and towards the target anatomy. The assembly 30, 130, 230, 330, 430, 530 and/or the probe 23 is manipulated such that the incident wave is reverberated with the reverberation feature 50, 150, 250, 350, 450, 550 to generate reflected waves (a, b, c, . . . ). For example, the assembly 30, 130, 230, 330, 430, 530 and/or the probe 23 may be manipulated to substantially align the reverberation feature 50, 150, 250, 350, 450, 550 with the incident wave (*). Further, the assembly 30, 130, 230, 330, 430, 530 and/or the probe 23 may be manipulated to alter the angle of approach θ to align the reverberation feature 50, 150, 250, 350, 450, 550. The method may include viewing on the display 26 the visual artifact (VA) generated with the ultrasound system 24 based on the reflected waves (a, b, c, . . . ). For example, assembly 30, 130, 230, 330, 430, 530 and/or the probe 23 may be manipulated to cause the visual artifact (VA) to intersect an axial position of the tumor (T). The assembly 30, 130, 230, 330, 430, 530 may be manipulated to cause the beveled tip 52, 152, 252, 352, 452, 552 and the distal end 64, 164, 264, 364 of the sheath 34, 134, 234, 334 to penetrate the tumor (T). Based on the visual artifact (VA) displayed on the display 26 and generated by the reverberation feature 50, 150, 250, 350, 450, 550 reverberating the waves, placement of the assembly 30, 130, 230, 330, 430, 530 (including the distal end 64, 164, 264, 364, 464, 564 of the sheath 34, 134, 234, 334, 434, 534) may be confirmed. Thereafter, the elongate body 32, 132, 232, 332 of the assembly 30, 130, 230, 330, 430, 530 may be removed from within the sheath 34, 134, 234, 334, 434, 534 while leaving the distal end 64, 164, 264, 364, 464, 564 of the sheath 34, 134, 234, 334, 434, 534 within the tumor (T). Any number of medical tasks may be performed using the sheath 34, 134, 234, 334, 434, 534 providing a conduit to an interior of the vessel, for example, a biopsy. In particular, a biopsy device (not shown) may be directed through the sheath 34, 134, 234, 334, 434, 534 to within the tumor (T). The biopsy device may have a length to be positioned just distal to the distal end 64, 164, 264, 364, 464, 564 of the sheath 34, 134, 234, 334, 434, 534 when a hub of the biopsy device engages the hub 40, 140, 240, 340, 440, 540, 640 of the sheath 34, 134, 234, 334, 434, 534. As a result, confident positioning of the distal end 64, 164, 264, 364, 464, 564 of the sheath 34, 134, 234, 334, 434, 534 from the reverberation feature 50, 150, 250, 350, 450, 550 provides for confident positioning of the biopsy device within the tumor (T). The biopsy device may be actuated to obtain the tissue sample.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A needle assembly positionable within anatomy of a patient under visual guidance from an ultrasound system, the needle assembly comprising:

a hub;

an elongate body extending from the hub along a longitudinal axis and comprising an inner surface defining a lumen, and a beveled tip; and reverberation features axially spaced proximal to the beveled tip and radially spaced relative to one another, wherein the reverberation features form a gap within the elongate body that is smaller than or shaped differently than the lumen.

2. The needle assembly of claim 1, wherein the reverberation features are exactly two reverberation features.

3. The needle assembly of claim 2, wherein the exactly two reverberation features are positioned on a superior aspect of the elongate body.

4. The needle assembly of claim 1, wherein the reverberation features are equiangularly spaced radially about the longitudinal axis.

5. The needle assembly of claim 1, wherein the reverberation features are notches.

6. The needle assembly of claim 5, wherein the notches are V-shaped in elevation.

7. The needle assembly of claim 1, wherein the reverberation features are crimps.

8. The needle assembly of claim 7, wherein the crimps comprise a proximal and distal transition portions separated by a reverberation portion.

9. The needle assembly of claim 1, wherein the reverberation features are arcuate contours.

10. The needle assembly of claim 1, further comprising a sheath, wherein the elongate body is removably positioned within the sheath.

11. The needle assembly of claim 10, wherein a distal end of the sheath is positioned proximal to the reverberation features.

12. A needle assembly positionable within anatomy of a patient under visual guidance from an ultrasound system, the needle assembly comprising:

a hub;

an elongate body extending from the hub along a longitudinal axis and defining a lumen, and a beveled tip;

a reverberation feature forming a gap within the elongate body that is smaller than or shaped differently than the lumen; and a sheath comprising a distal end axially spaced proximal to the reverberation feature, wherein the elongate body is configured to be removably positioned within the sheath.

13. The needle assembly of claim 12, wherein the reverberation feature is at least one of a notch, a crimp, and an arcuate contour.

14. The needle assembly of claim 12, wherein the reverberation feature comprises more than one reverberation features equiangularly spaced radially about the elongate body.

15. The needle assembly of claim 14, where the reverberation features are axially located at a common axial position along the elongate body.

16. A needle assembly positionable within anatomy of a patient under visual guidance from an ultrasound system, the needle assembly comprising:

a hub;

an elongate body extending from the hub along a longitudinal axis and defining a lumen; and reverberation features axially located at a common axial position along the elongate body, wherein the reverberation features form a gap within the elongate body that is smaller than or shaped differently than the lumen.

17. The needle assembly of claim 16, wherein the reverberation features are equiangularly spaced radially about the elongate body.

18. The needle assembly of claim 17, further comprising additional reverberation features located at another common axial position to provide ring-like arrangements of groups of the reverberation features.

19. The needle assembly of claim 16, further comprising a sheath, wherein the elongate body is removably positioned within the sheath.

20. The needle assembly of claim 19, wherein a distal end of the sheath is spaced proximal to the reverberation features.

* * * * *